ns010758428B2

United States Patent
Nakamura et al.

(10) Patent No.: US 10,758,428 B2
(45) Date of Patent: Sep. 1, 2020

(54) STRETCHABLE SHEET, WORN ARTICLE USING THE SAME, AND STRETCHABLE SHEET MANUFACTURING APPARATUS

(71) Applicant: ZUIKO CORPORATION, Osaka (JP)

(72) Inventors: Hideyuki Nakamura, Osaka (JP); Miwa Koshijima, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 0 days.

(21) Appl. No.: 16/330,081

(22) PCT Filed: Sep. 7, 2017

(86) PCT No.: PCT/JP2017/032318
§ 371 (c)(1),
(2) Date: Mar. 2, 2019

(87) PCT Pub. No.: WO2018/070150
PCT Pub. Date: Apr. 19, 2018

(65) Prior Publication Data
US 2019/0224053 A1    Jul. 25, 2019

(30) Foreign Application Priority Data

Oct. 11, 2016   (JP) ................. 2016-199926

(51) Int. Cl.
*A61F 13/49*     (2006.01)
*B32B 3/28*      (2006.01)
(Continued)

(52) U.S. Cl.
CPC ........ *A61F 13/49009* (2013.01); *A61F 13/49* (2013.01); *B32B 3/28* (2013.01);
(Continued)

(58) Field of Classification Search
CPC ............... A61F 13/49009; A61F 13/49; A61F 2013/51429; A61F 2013/51322;
(Continued)

(56) References Cited

U.S. PATENT DOCUMENTS

| 2014/0302286 | A1* | 10/2014 | Okuda .................... B32B 3/28 428/184 |
| 2016/0067115 | A1* | 3/2016 | Ishikawa ........... A61F 13/15593 428/181 |
| 2017/0281417 | A1 | 10/2017 | Ishikawa |

FOREIGN PATENT DOCUMENTS

| JP | 2010-260323 A | 11/2010 |
| JP | 2012-120775 A | 6/2012 |

(Continued)

OTHER PUBLICATIONS

International Search Report Issued in PCT/JP2017/032318 dated Dec. 12, 2017 (with English translation).

*Primary Examiner* — David Sample
*Assistant Examiner* — Donald M Flores, Jr.
(74) *Attorney, Agent, or Firm* — Renner, Otto, Boisselle & Sklar, LLP

(57) ABSTRACT

A stretchable sheet 10 includes: a plurality of attached portions 3 spaced apart from each other in the direction of stretch Df, wherein the first surfaces 1f and 2f of a pair of sheets 1 and 2 are attached to each other by being welded without using an adhesive, at the attached portions 3, the attached portions 3 hold elastic members F, and the attached portions 3 extend in a direction Dp crossing the direction of stretch Df of the elastic members F; and a plurality of folds P that appear between the attached portions 3 while the elastic members F are shrunk, wherein a width W3 of the attached portions 3 in the direction of stretch Df is set to be 0.2 mm or more and less than 1.0 mm.

6 Claims, 20 Drawing Sheets

(51) Int. Cl.
  *A61F 13/513*  (2006.01)
  *A61F 13/514*  (2006.01)
  *B32B 7/05*  (2019.01)

(52) U.S. Cl.
  CPC ............... *A61F 2013/51322* (2013.01); *A61F 2013/51429* (2013.01); *B32B 7/05* (2019.01); *B32B 2555/02* (2013.01); *Y10T 428/24* (2015.01); *Y10T 428/24025* (2015.01); *Y10T 428/24033* (2015.01)

(58) Field of Classification Search
  CPC .. A61F 2013/15878; A61F 2013/49023; A61F 13/51476; A61F 13/51464; A61F 13/513; A61F 13/51104; A61F 13/15747; A61F 13/15593; A61F 16/15699; A61F 13/4902; B32B 3/28; B32B 7/05; B32B 2555/02; Y10T 428/24025; Y10T 428/24033; Y10T 428/24
  See application file for complete search history.

(56) References Cited

FOREIGN PATENT DOCUMENTS

| | | |
|---|---|---|
| JP | 2014-198180 A | 10/2014 |
| JP | 2015-058226 A | 3/2015 |
| JP | 2016-005545 A | 1/2016 |
| JP | 2016-067436 A | 5/2016 |
| WO | WO 2014-156949 A1 | 10/2014 |

\* cited by examiner

FIG. 2
(a)
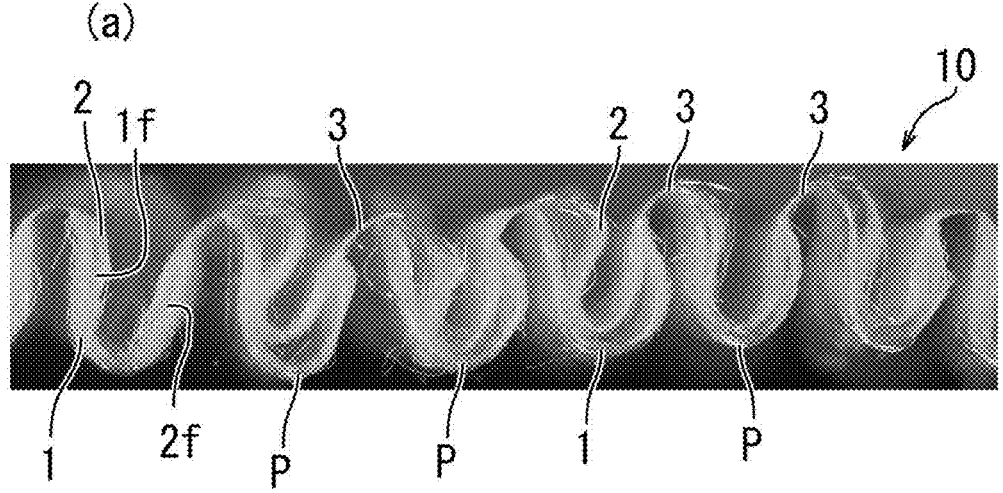
(b)
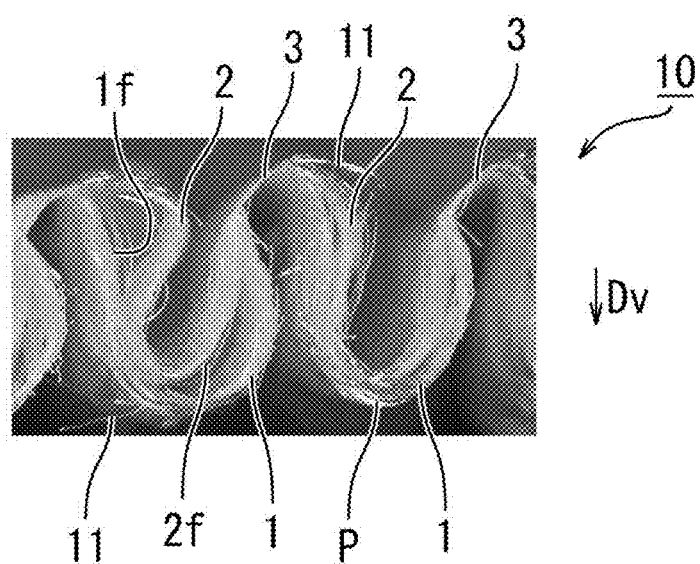

FIG. 3
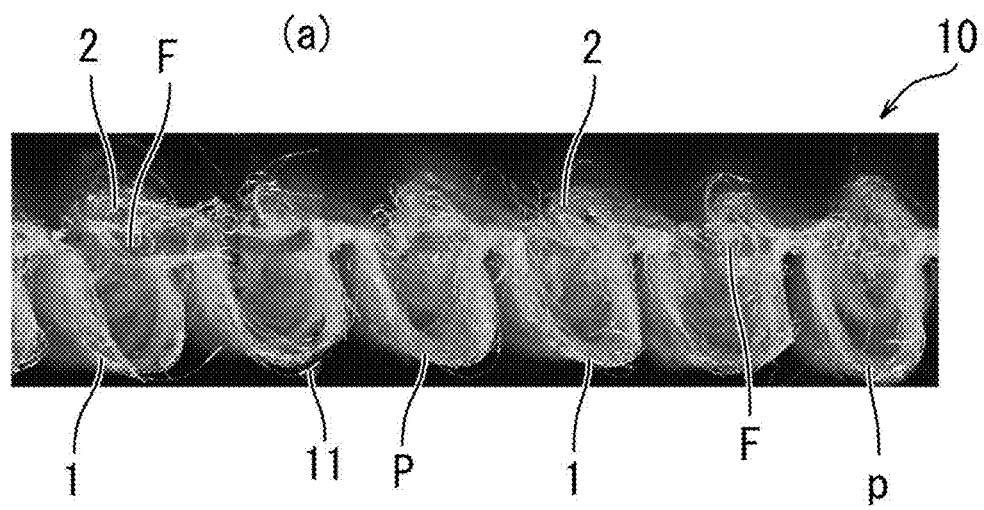
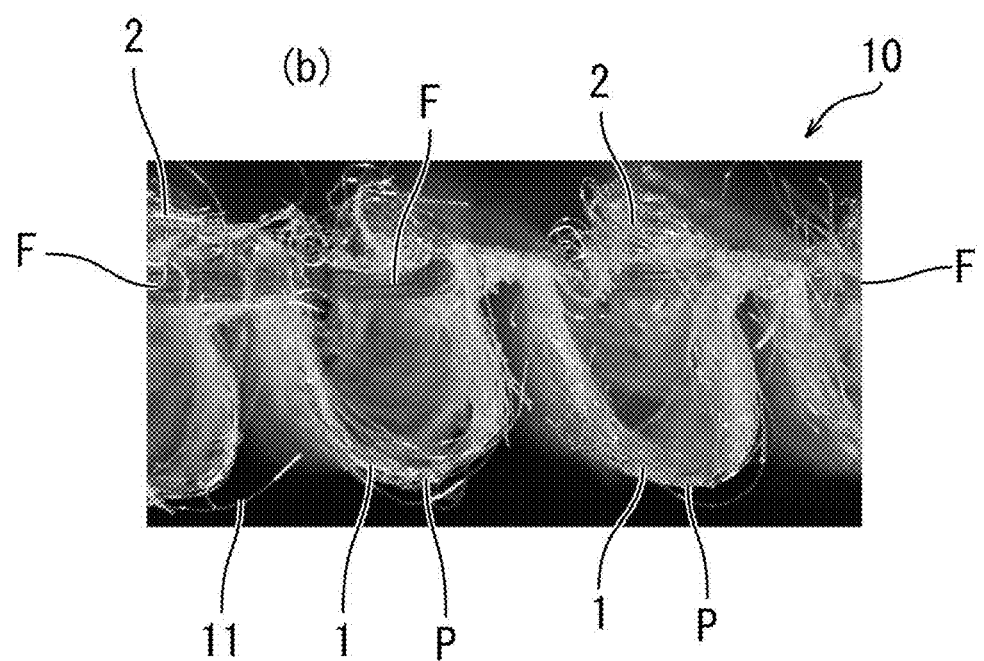

FIG. 5
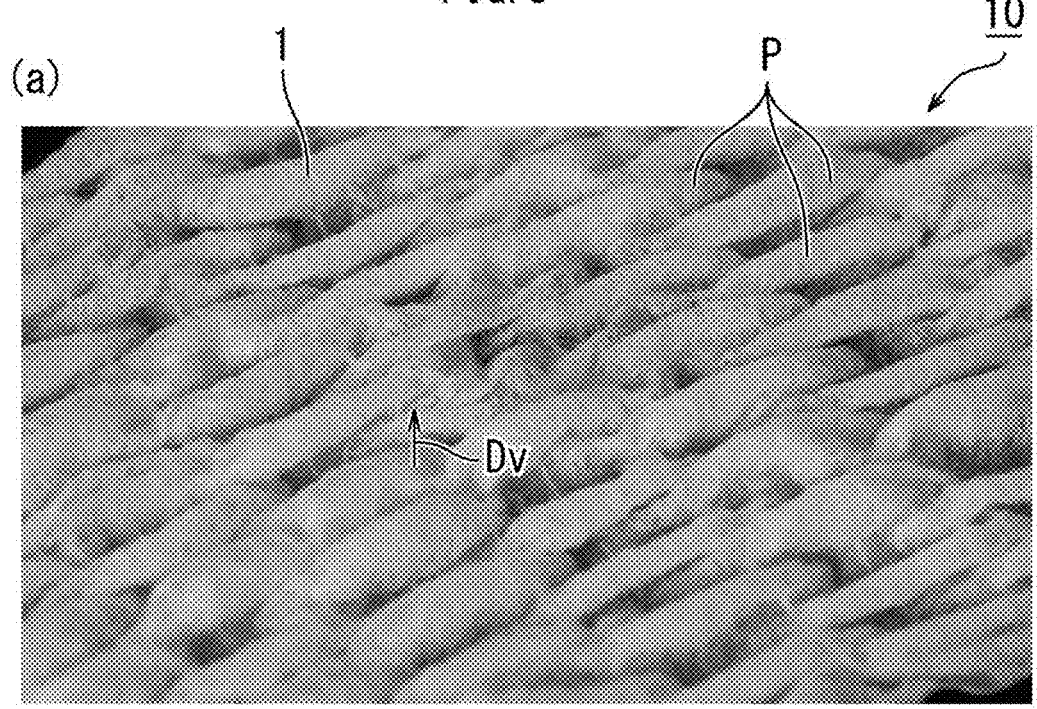
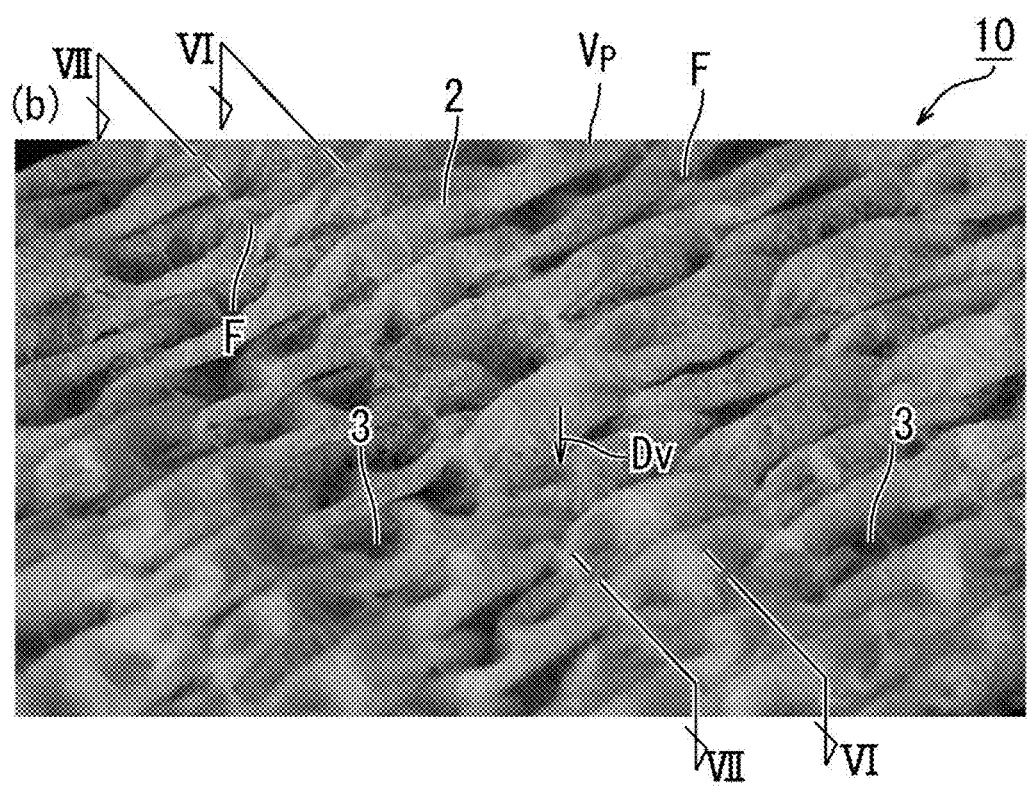

FIG. 6
(a)
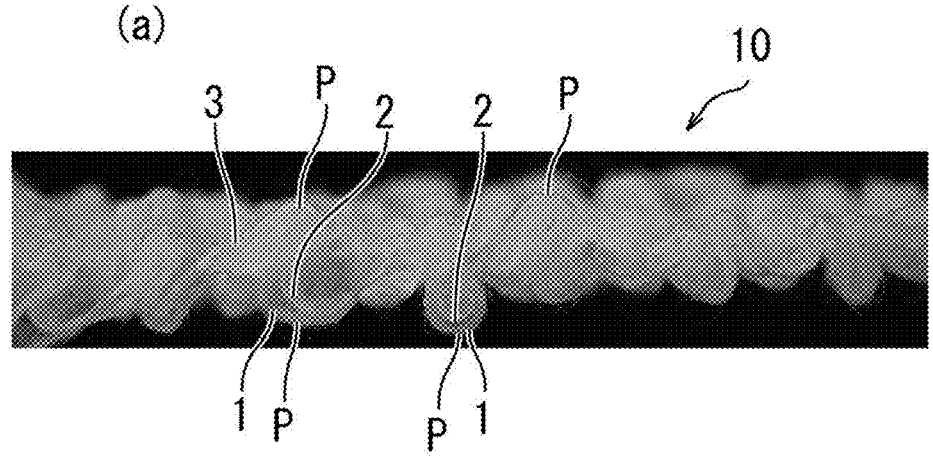
(b)
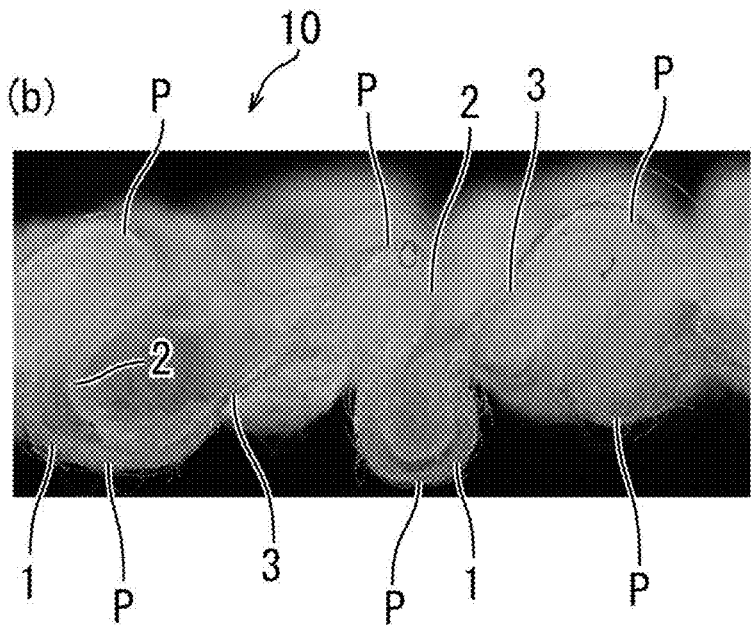

FIG. 7
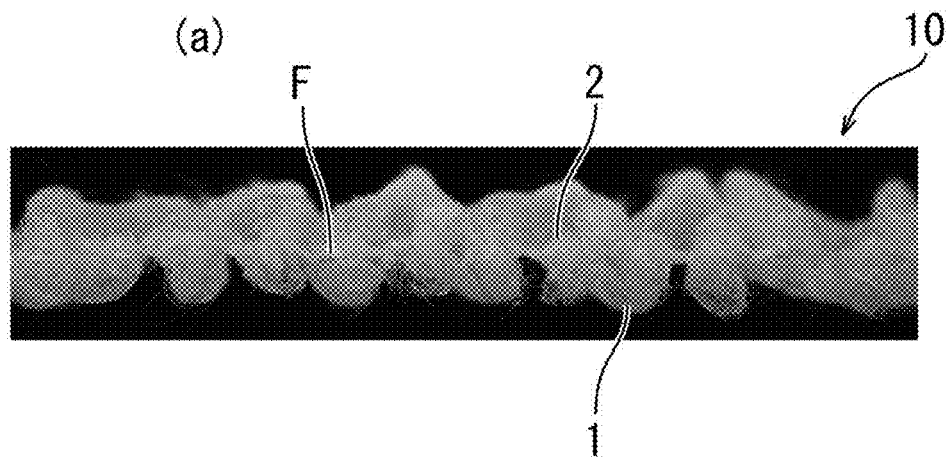
(a)
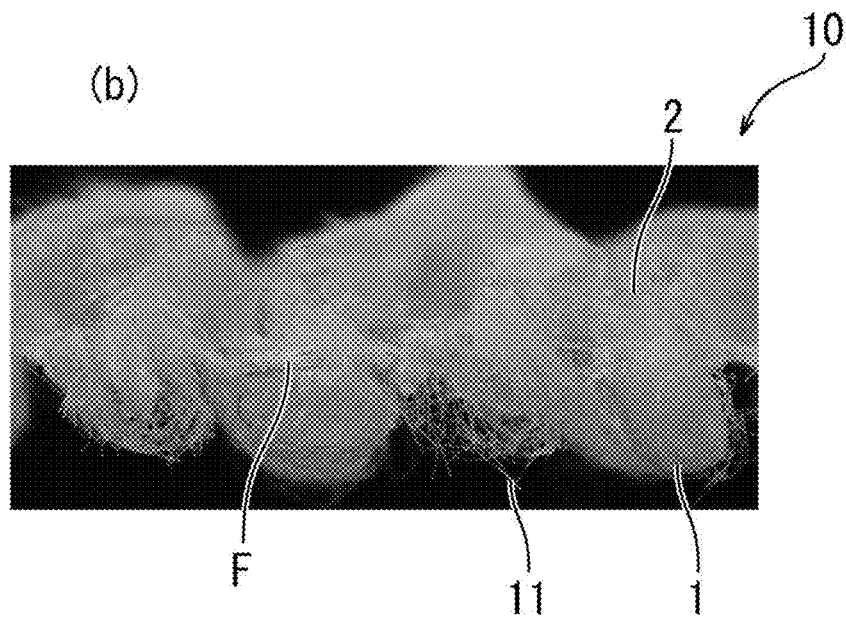
(b)

FIG.9
(a) 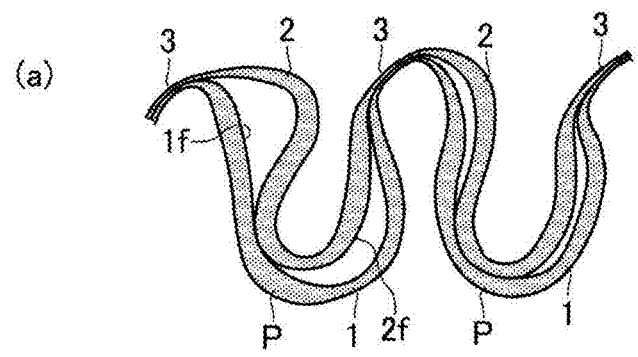
(b) 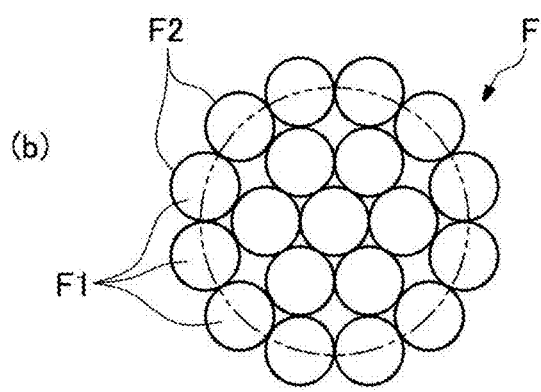
(c) 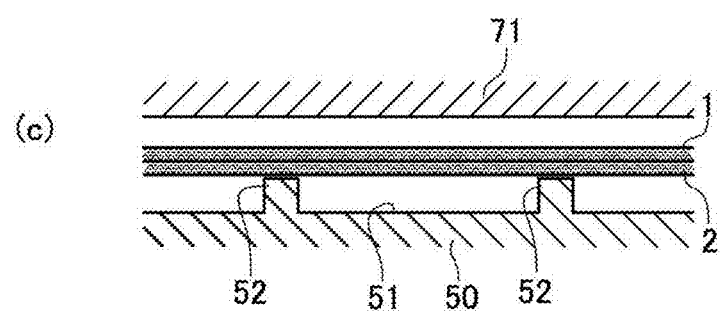

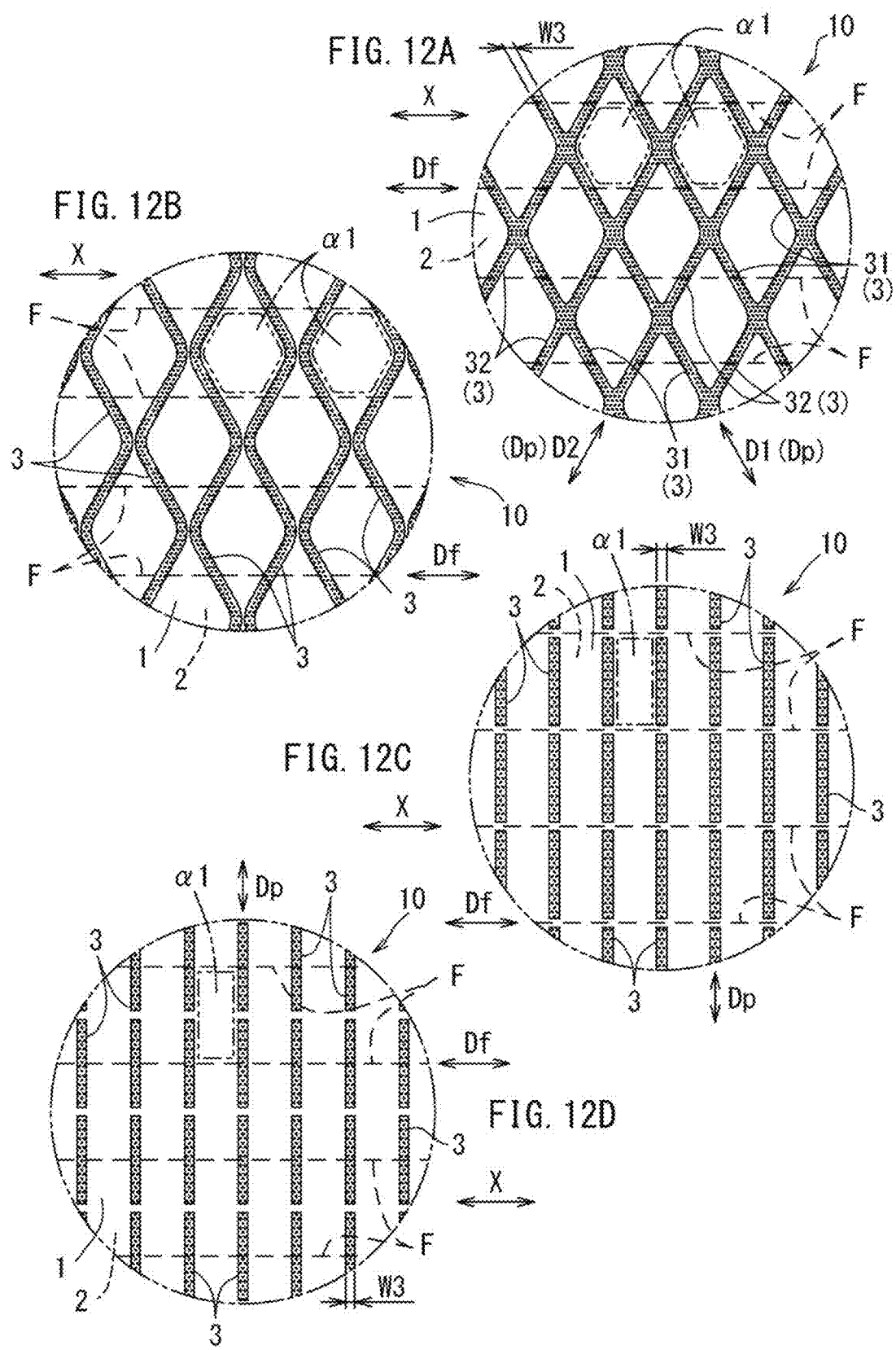

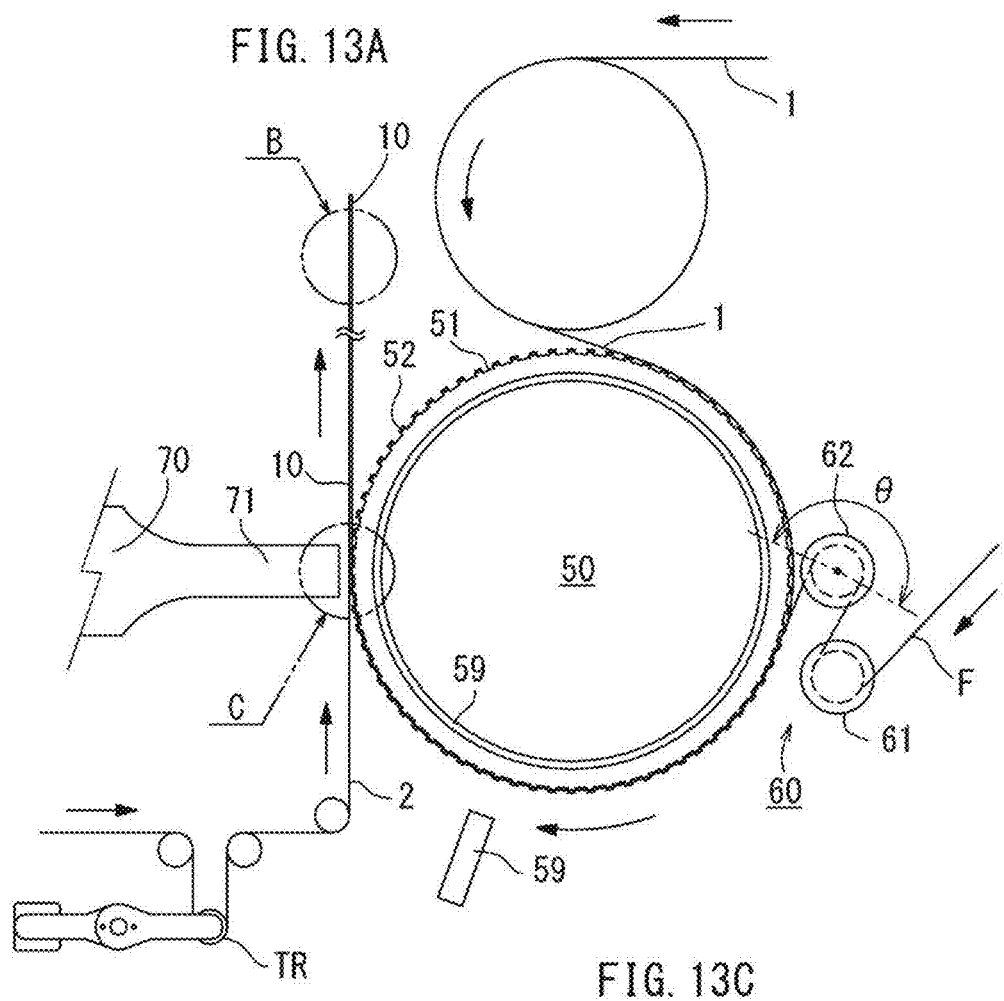
FIG. 13A
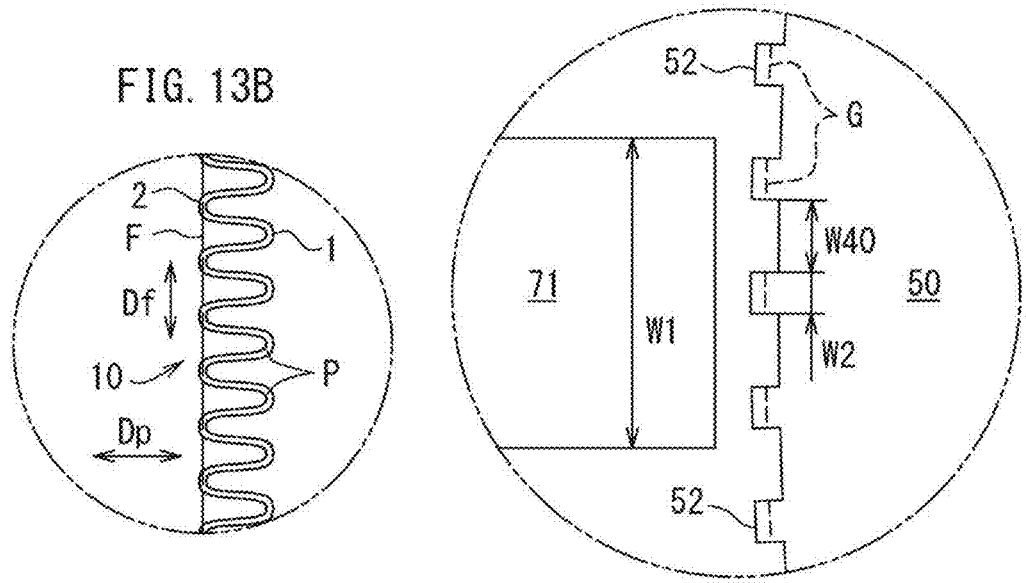
FIG. 13B
FIG. 13C

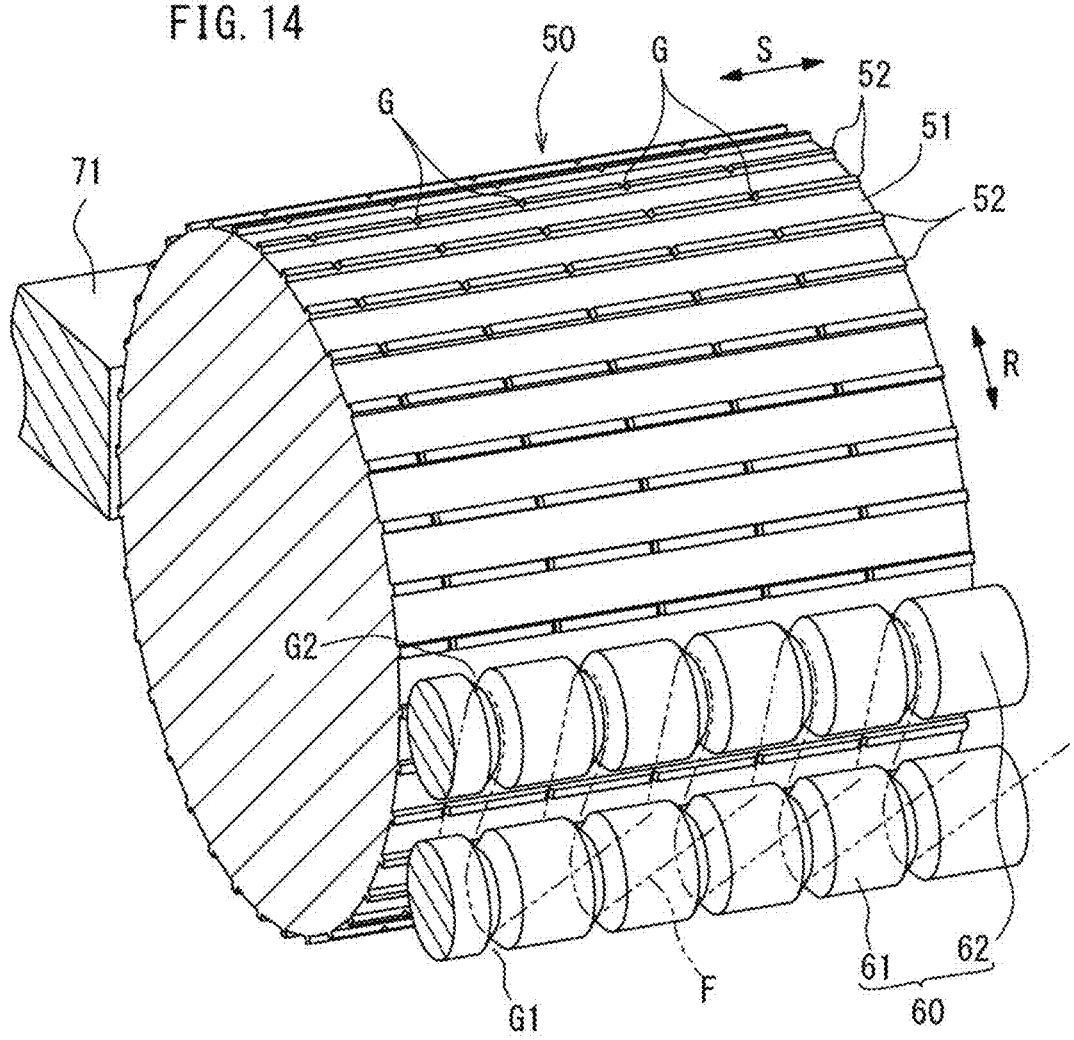

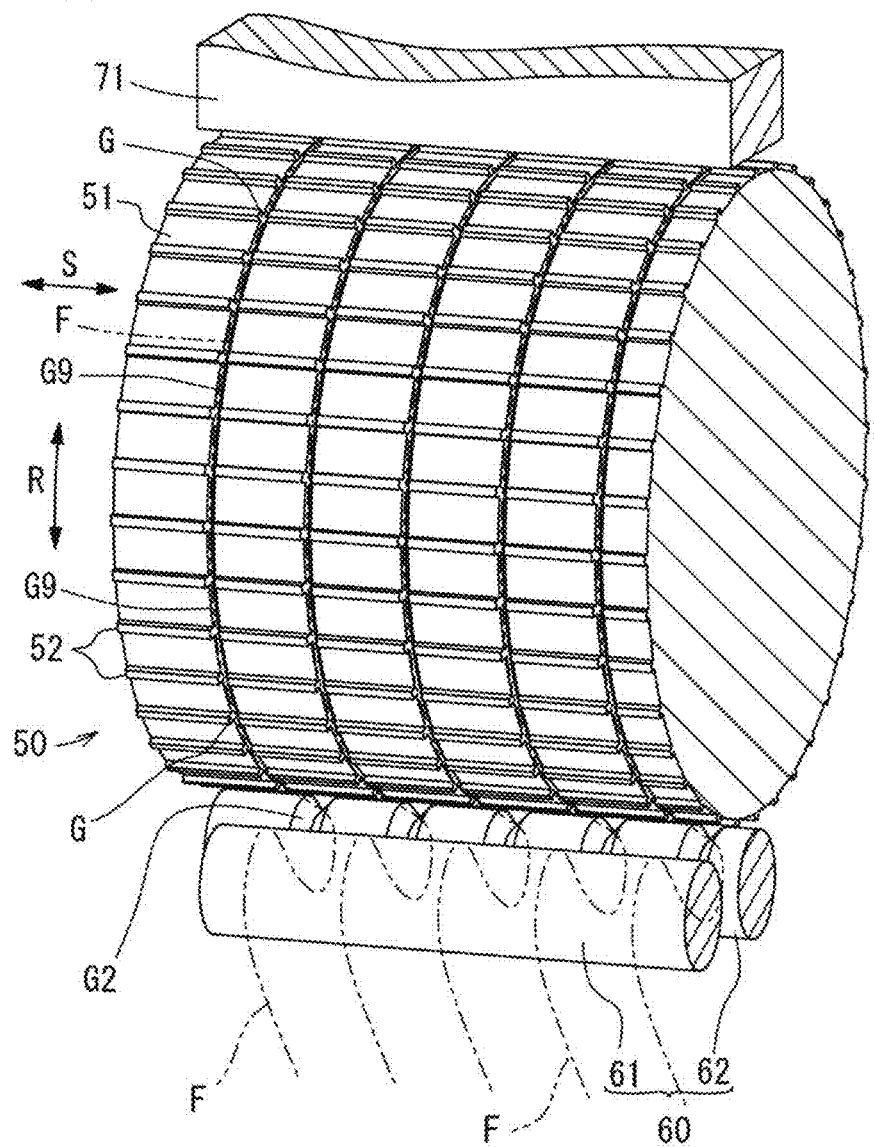
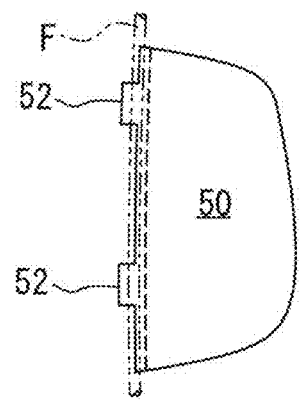
FIG. 17A
FIG. 17B

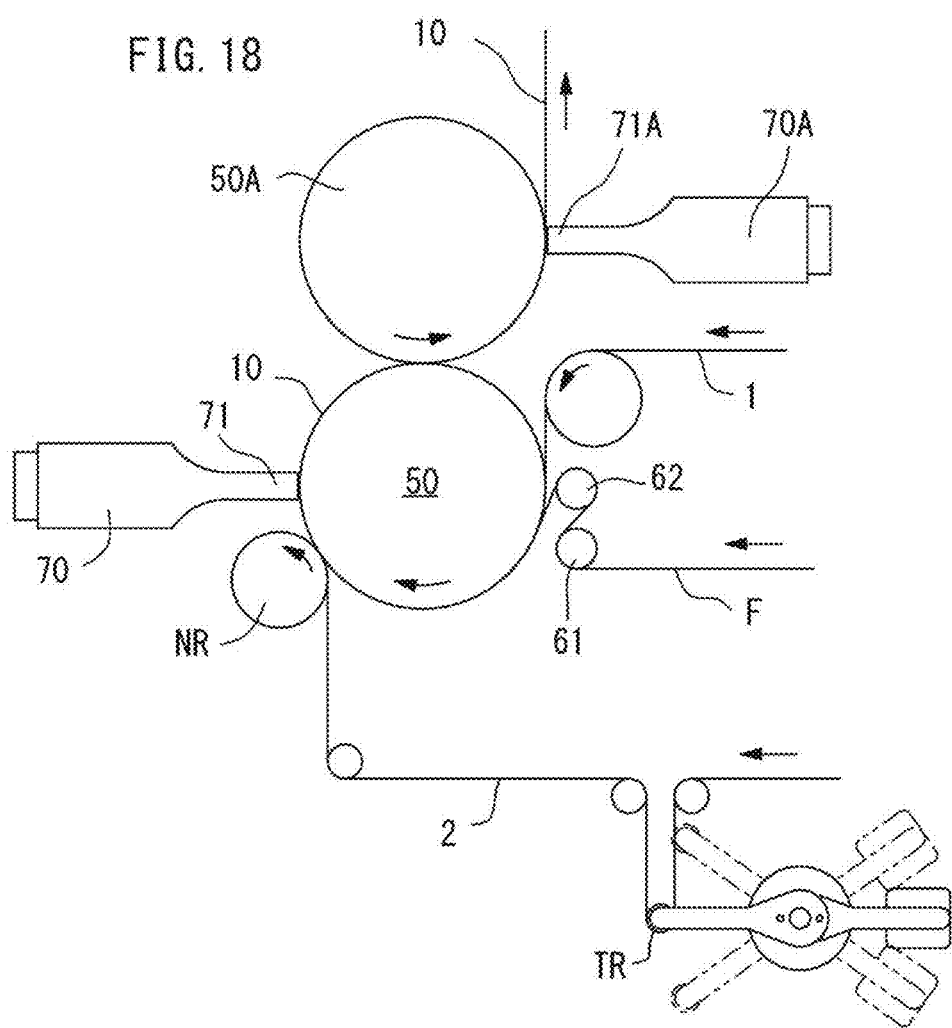

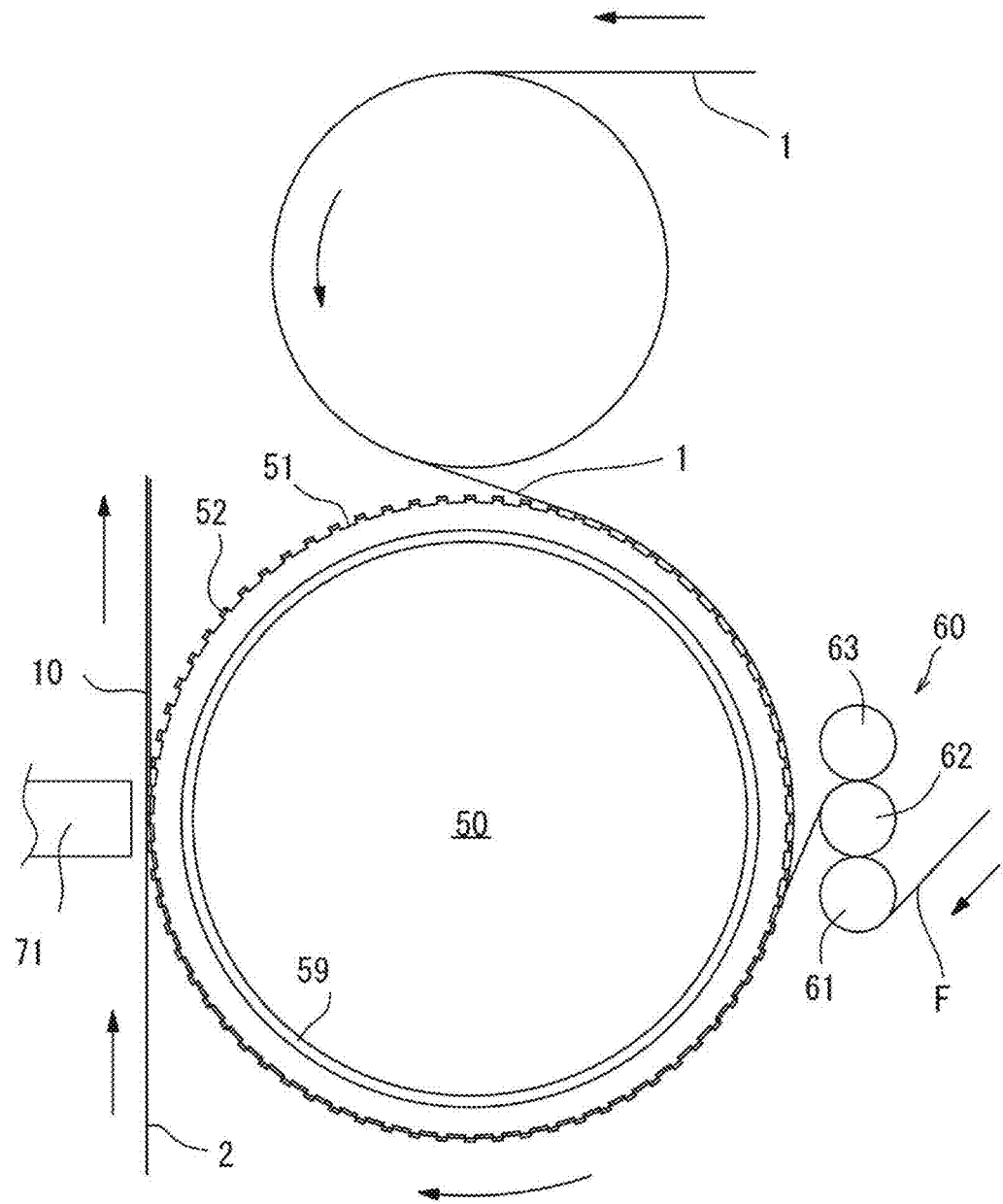

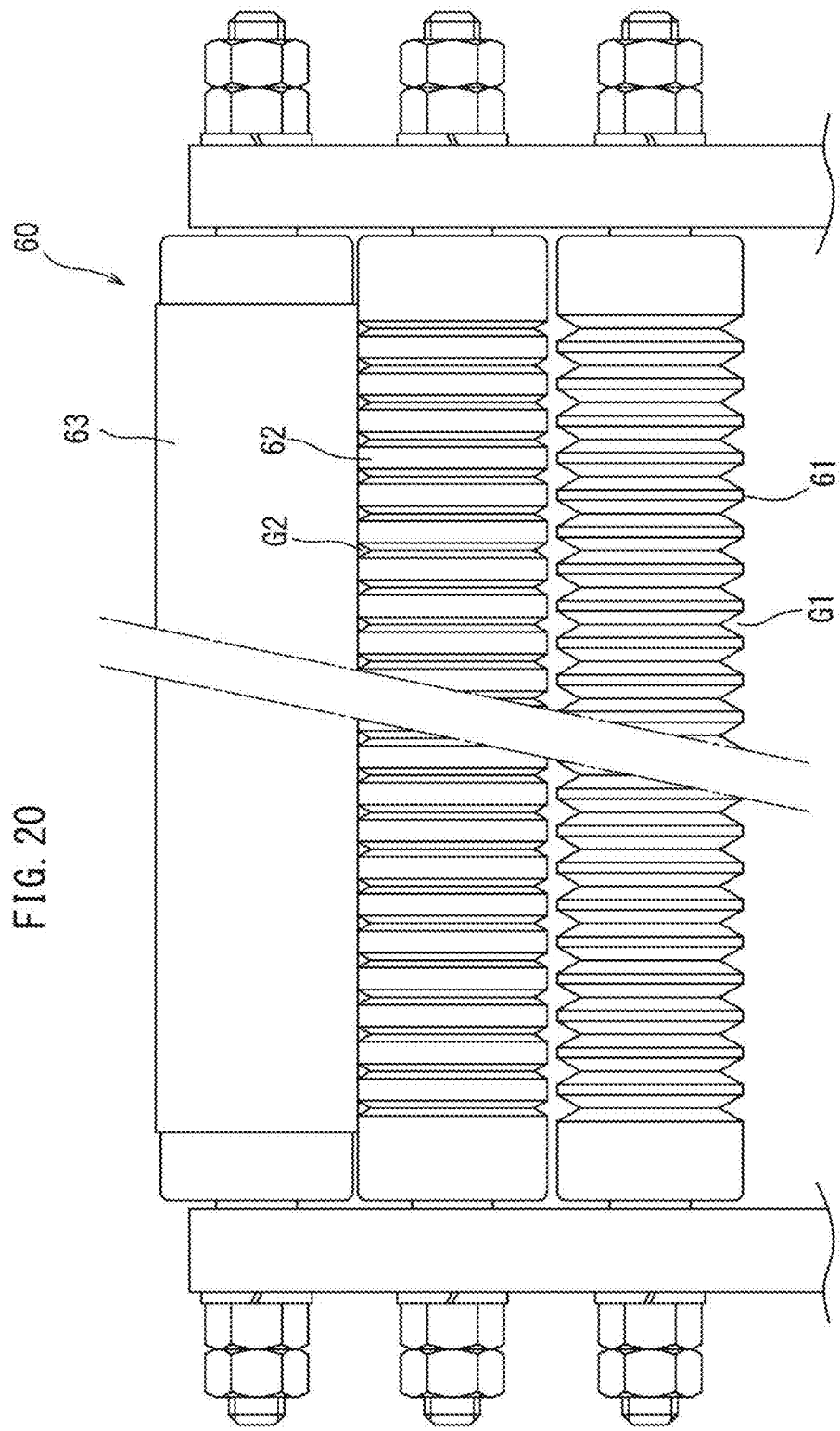

STRETCHABLE SHEET, WORN ARTICLE USING THE SAME, AND STRETCHABLE SHEET MANUFACTURING APPARATUS

TECHNICAL FIELD

The present invention relates to a stretchable sheet, a worn article using the same, and a stretchable sheet manufacturing apparatus.

BACKGROUND ART

A structure in which a plurality of elastic members are sandwiched between two sheets, wherein the two sheets are welded together and elastic members are secured between the two sheets at attached portions that extend in a direction crossing the direction of stretch of the elastic members, is known in the art as a structure of a stretchable sheet (first patent document).

CITATION LIST

Patent Literature

[First Patent Document] JP2014-198180A (front page)

SUMMARY OF INVENTION

One method for securing elastic members is a method of pressing sheets against the elastic members while the sheets are heated. If one increases the width of the attached portions in order to firmly secure the elastic members on the sheets, the sheets will be heated with an increased surface pressure over a wide attachment range. In such a case, the elastic members may be possibly excessively pressurized and heated to be broken. This will likely lower the production yield and the quality of the stretchable sheet.

Thus, it is an object of the present invention to provide a stretchable sheet, a worn article and a stretchable sheet manufacturing apparatus, with which it is possible to reduce securing failure and breakage of the attached portions, thereby improving the production yield and the quality of the product.

That is, a stretchable sheet of the present invention includes: a pair of sheets 1 and 2, wherein a first surface 1*f* of one of the pair of sheets and a first surface 2*f* of another one of the pair of sheets oppose (face) each other or are in contact with each other;

a plurality of elastic members F that are arranged between the first surfaces 1*f* and 2*f* of the pair of sheets 1 and 2 and are arranged spaced apart from each other;

a plurality of attached portions 3, wherein the first surfaces 1*f* and 2*f* of the pair of sheets 1 and 2 are attached to each other by a welding construction (a welded structure) without using an adhesive, at the attached portions 3; the attached portions 3 hold the elastic members F; the attached portions 3 extend in a direction Dp crossing a direction of stretch Df of the elastic members F; and the attached portions 3 are spaced apart from each other in the direction of stretch Df at positions where the attached portions 3 cross the elastic members F; and a plurality of folds (pleats) P that appear between the attached portions 3 in a state where the elastic members F are shrunk, wherein a width W3 of the attached portions 3 (each attached portion 3) in the direction of stretch Df is set to be 0.2 mm or more and less than 1.0 mm.

On the other hand, a stretchable sheet manufacturing apparatus of the present invention includes:

an anvil roll 50 for carrying the pair of sheets 1 and 2 and the elastic members F so that the elastic members F are arranged between the pair of sheets 1 and 2; and a welding device 70, in cooperation with the anvil roll 50, for welding together the pair of sheets 1 and 2 so that the elastic members are held by the pair of sheets, wherein:

the anvil roll 50 has a plurality of ridges 52 that are formed on a circumferential surface 51 of the anvil roll 50 and extend in a width direction S of the anvil roll 50;

the ridges 52 define carrying grooves G that extend in a circumferential direction of the anvil roll 50 for carrying the elastic members F with a portion of one of the pair of sheets 1 and 2 and elastic members F being held in the carrying grooves G; and a width W2 of the ridges 52 (each ridge 52) in a direction in which the elastic members F are carried is set to be 0.2 mm or more and less than 1.0 mm.

According to the present invention, the elastic members are pressurized while being accommodated in the carrying grooves. However, if the width of the attached portions or the width of the ridges is large, the carrying grooves become long, and the elastic members are likely to partially lie outside the carrying grooves to be under an excessive pressure. In contrast, with the width being narrow, the carrying grooves become short so that the elastic members are likely to be accommodated in the carrying grooves, and the elastic members will be prevented from breaking as an excessive pressure is released.

The elastic members move at a constant speed, and therefore individual portions thereof are each heated for a constant amount of time regardless of the width. However, if the width is large, the portion to be heated becomes continuously long. Therefore, heat is accumulated, and the sheets and the elastic members may possibly be heated excessively.

Now, the width W3 of the attached portions 3 in the direction of stretch being 0.2 mm or more and less than 1.0 mm means that the width W3 of the attached portions is 0.2 mm or more and less than 1.0 mm at least at positions where they cross the elastic members, and between the elastic members, the width W3 is 0.2 mm or more and less than 1.0 mm for more than a half (greater than or equal to a half) the length of the attached portions 3 in the longitudinal direction. Preferably, the width W3 is set to be 0.2 mm or more and less than 1.0 mm for the majority (80% or more) of the attached portions 3 in the longitudinal direction.

That is, the width W3 of the attached portions 3 may be partly 1.0 mm or more. For example, in a case where two lines of the attached portion cross each other, the width W3 of the attached portion 3 at the intersection may be 1.0 mm or more.

On the other hand, the width W3 of the attached portions 3 may be partly less than 0.2 mm. For example, in a case where the attached portions are provided intermittently in the longitudinal direction, there will be portions where the width is substantially 0 mm.

The concept of the width W3 of the attached portions 3 described above applies similarly to the width W2 of the ridges.

For example, the width W2 of the ridges being 0.2 mm or more and less than 1.0 mm means that the width W2 of the ridges is 0.2 mm or more and less than 1.0 mm at least at positions where the carrying grooves are provided, and that the width W2 is 0.2 mm or more and less than 1.0 mm for more than a half (greater than or equal to a half) the length of the ridges in the longitudinal direction of the ridges. Preferably, the width of the width W2 is set to be 0.2 mm or more and less than 1.0 mm for the majority (80% or more) of the ridges in the longitudinal direction of the ridges.

That is, the width of the ridges may be partly less than 0.2 mm or 1.0 mm or more.

On the other hand, the depth of the carrying grooves may be the same as the height of the ridges, or may be less than the height of the ridges, and may in some cases be greater than the height of the ridges.

Preferably, the welding device includes an ultrasonic horn 71 that opposes the ridges 52 with the pair of sheets 1 and 2 and the elastic members F interposed therebetween, wherein an ultrasonic energy is given to the ultrasonic horn 71; and a width W1 of the horn 71 along a direction in which the sheets flow is greater than the width W2 of the ridges 52.

In this case, the width of the attached portions or the width of the ridges of the anvil roll is small as it is set to be 0.2 mm or more and less than 1.0 mm. Therefore, an excessive pressure is unlikely to be applied to the elastic members in the attached portions. As a result, the production yield of the stretchable sheet will improve.

The width of the attached portions whose stretchability is lost is narrow, and the stretchable sheet, which is formed from a pair of sheets that are welding to each other, will have a good stretchability. Therefore, the quality of the product will improve.

The attached portions harden as they melt at at least some portions of the stretchable sheet. However, the area of the attached portions is small, and the flexibility of the stretchable sheet is maintained. The width of the attached portions being narrow also contributes to the improvement of the flexibility.

Since the width of the attached portions or the ridges is narrow, the interval between folds to be formed when the stretchable sheet is shrunk will be narrow. Therefore, since the folds are formed with a high density, the feel and the look of the stretchable sheet will also be good.

BRIEF DESCRIPTION OF DRAWINGS

FIGS. 2(a) and 2(b) are an enlarged cross-sectional view and a more enlarged cross-sectional view, respectively, showing digital photographs of cross sections obtained by severing the stretchable sheet along line II-II of FIG. 1(b) by scissors.

FIGS. 3(a) and 3(b) are an enlarged cross-sectional view and a more enlarged cross-sectional view, respectively, showing digital photographs of cross sections obtained by severing the stretchable sheet along line III-III of FIG. 1(b) by scissors.

FIGS. 5(a) and 5(b) are enlarged perspective views showing digital photographs of a first outer surface and a second outer surface, respectively, according to Embodiment 2 of the present invention.

FIGS. 6(a) and 6(b) are an enlarged cross-sectional view and a more enlarged cross-sectional view, respectively, showing digital photographs of cross sections obtained by severing the stretchable sheet along line VI-VI of FIG. 5(b) by scissors.

FIGS. 7(a) and 7(b) are an enlarged cross-sectional view and a more enlarged cross-sectional view, respectively, showing digital photographs of cross sections obtained by severing the stretchable sheet along line VII-VII of FIG. 5(b) by scissors.

FIG. 9(a) is a cross-sectional view showing a drawing of the cross section of the stretchable sheet of FIG. 2(b), FIG. 9(b) is a cross-sectional view showing elastic strands, and FIG. 9(c) is a cross-sectional view showing a pair of sheets in an unwelded state.

FIG. 12A, FIG. 12B, FIG. 12C and FIG. 12D are enlarged plan views showing, flattened, Embodiments 2, 3, 4 and 5, respectively, of the stretchable sheet.

FIG. 13A is a layout diagram showing a manufacturing apparatus of the present invention, FIG. 13B is an enlarged conceptual diagram of the B part, and FIG. 13C is an enlarged side view of the C part.

FIG. 14 is a schematic perspective view of the anvil roll as seen from the introduction device side.

FIG. 17A is a schematic perspective view showing another example of the anvil roll, and FIG. 17B is an enlarged side view showing a portion of the anvil roll.

FIG. 18 is a schematic layout diagram showing another example of the manufacturing apparatus.

FIG. 19 is a schematic layout diagram showing another example of the introduction device.

FIG. 20 is a front view of the introduction device.

In FIGS. 9(a) and 9(c) and FIG. 10, non-woven fabric sheet portions are shown in gray. The attached portions of FIG. 11B to FIG. 12D are dotted.

DESCRIPTION OF EMBODIMENTS

Figure 1:
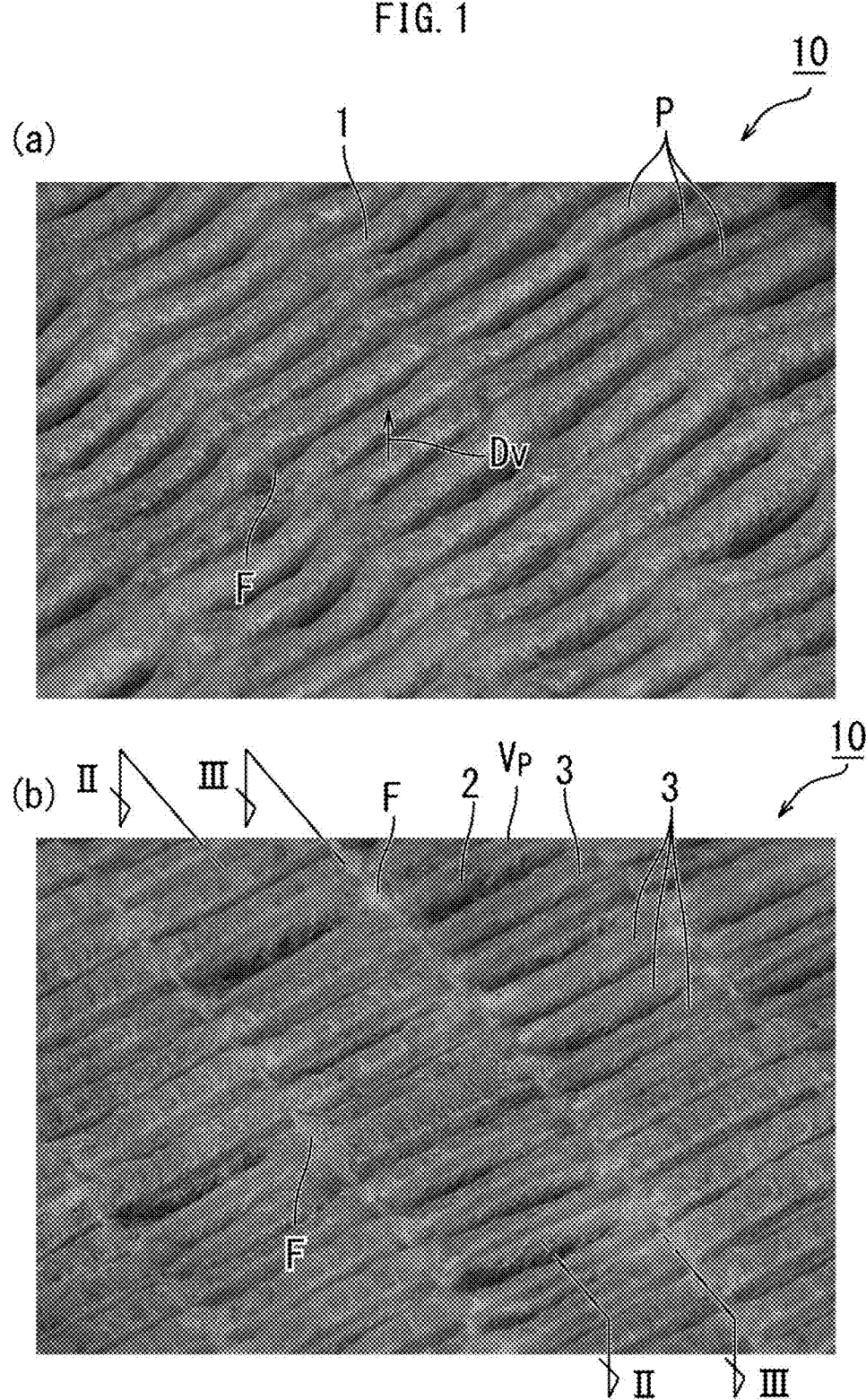
FIGS. 1(a) and 1(b) are enlarged perspective views showing digital photographs of a first outer surface and a second outer surface, respectively, according to Embodiment 1 of the stretchable sheet of the present invention.

The unwelded, non-attached portions of the sheets of the conventional technique bulge in opposite directions through shrinking of the elastic members, thereby forming folds. The folds of the conventional technique are each made of a single sheet. Therefore, the folds of the conventional technique are likely to easily collapse under an external force. For example, when the stretchable sheet of the conventional technique is used in a worn article, it is difficult to maintain the shape of the folds, and the texture and the feel are likely to deteriorate.

In view of this, a preferred example of the present invention provides a stretchable sheet whose folds are less likely to collapse under an external force.

That is, in a preferred stretchable sheet, the pair of sheets 1 and 2 protrude, between the attached portions 3, with respect to a virtual plane Vp that includes the elastic members F; and in an area α1 defined between adjacent attached portions 3 and adjacent elastic members F, non-bonded positions of the pair of sheets 1 and 2 that oppose each other protrude in the same direction, thereby forming a fold P.

With such a stretchable sheet, in the area α1, the positions of the pair of sheets that oppose each other protrude in the same direction, thereby forming the folds. Therefore, one sheet and the other sheet that form each fold are layered together. Thus, the fold positions are unlikely to collapse under an external force. Moreover, the appearance is unlikely to be disturbed.

Since the sheets in each fold protrude in the same direction, the thickness of the stretchable sheet will be thin.

In the present invention, "the positions of the pair of sheets that oppose each other protrude in the same direction" means that one position of one sheet and the same position of the other sheet that oppose each other protrude in one same direction, and another position of one sheet and the same position of the other sheet that oppose each other may protrude in another same direction.

In the present invention, "non-bonded positions" means to exclude cases where the sheets are bonded together via an adhesive, which detracts from the air-permeability or the texture of the folds.

When the pair of sheets that hold the elastic members F are non-woven fabric sheets, a large number of fibers may be stuck on the elastic members F as if by tangling with the elastic members F, or some or all of a large number of fibers may be welded to the elastic members F.

Each attached portion does not need to be one completely continuous portion, but may intermittently extend in the crossing direction Dp. For example, the attached portions may be broken between adjacent elastic members F, or may be broken at positions where the elastic members F are arranged.

With the present manufacturing apparatus, the width of the ridges of the anvil roll is 0.2 mm or more and less than 1.0 mm, and the width of the ridges of the anvil roll is narrower than the width of the horn. Since the width of the ridges is less than 1 mm, the sheets, when pressurized, are likely to both deform toward the anvil roll on both sides in the width direction of the ridges, and the folds are likely to be formed with the sheets both protruding in the same direction.

That is, when the width of the ultrasonic horn in the flow direction is greater than the width of the ridges of the anvil in the flow direction, the sheets, when being welded, are likely to be displaced into the space between ridges, and it is expected that the sheets are likely to both bulge in the same direction.

When being sealed, portions of the sheets may be displaced into between ridges, and the sheets may be likely to bulge in the same direction.

In a preferred manufacturing apparatus for obtaining such a stretchable sheet, one of the pair of sheets 1 and 2 is the first sheet 1 to be in contact with the anvil 50 and another one of the pair of sheets 1 and 2 is the second sheet 2 to be in contact with the horn 71; and the manufacturing apparatus includes a tension roller TR upstream of the horn 71 for making a tension of the second sheet 2 in a carrying direction higher than a tension of the first sheet 1 in the carrying direction.

When the first and second sheets are welded, the sheets soften at the attached portions. Therefore, no tension remains on the sheets at the attached portions. On the other hand, at the non-attached portions, a tension difference between the sheets remains, and the horn-side second sheet having a greater tension is more likely to shrink after welding than the anvil-side first sheet. As a result, a plurality of folds are likely to protrude in the same direction.

Preferably, at least one of the pair of sheets 1 and 2 is welded to the elastic members F at the attached portions 3.

In this case, the holding of the elastic members by the pair of sheets that are welded to the elastic members becomes even more stable.

Preferably, the first surfaces 1f and 2f of the pair of sheets 1 and 2 are in contact with each other at at least some of the positions that oppose each other to form the folds P.

In this case, the pair of sheets 1 and 2 are non-bonded at positions where folds are formed, and the flexibility of the stretchable sheet is therefore not lost. The folds where the first surfaces are at least partly in contact with each other, the 2-layer structure portions increase the flexural rigidity of the folds. That is, dynamically speaking, the flexural rigidity is in proportion to the cube of the thickness of the material, and folds that are formed from a soft material are therefore unlikely to collapse.

Preferably, the attached portions 3 are formed in straight lines parallel to each other; and the folds P are formed in straight lines parallel to each other along the attached portions 3 that are parallel to each other.

In this case, since the folds are formed in straight lines parallel to each other, the folds appear in straight lines on the surface on which the folds protrude, and it will be possible to obtain a stretchable sheet with a beautiful appearance.

Preferably, the attached portions 3 include a plurality of first attached portions 31 that extend in a first direction D1 crossing the direction of stretch Df of the elastic members F, and a plurality of second attached portions 32 that extend in a second direction D2 crossing the direction of stretch Df and the first direction D1.

The area α1 is defined by the elastic members F, the first attached portions 31 and the second attached portions 32.

In this case, various stripe-shaped folds are obtained depending on the setting of the first and second directions.

One preferred worn article has a skin-contact surface to be in contact with a skin of a wearer, and a non-skin-contact surface that is opposite thereto; and the folds P protrude on the non-skin-contact surface.

When the side on which the folds protrude is the non-skin-contact side of the worn article as described above, the texture of the non-skin-contact surface is good. Moreover, the contact area between the skin-contact surface side and the skin of a wearer will be small, thereby preventing stuffiness.

Another preferred worn article has a skin-contact surface to be in contact with a skin of a wearer, and a non-skin-contact surface that is opposite thereto; and the folds P protrude on the skin-contact surface.

In this case, the folds protruding on the skin-contact surface are unlikely to collapse, thereby resulting in a good wearability.

A preferred manufacturing apparatus further includes a heating device 59 for heating one of the pair of sheets that is in contact with the anvil 50.

In ultrasonic welding, if the width of the attached portions is narrow, the heat capacity to be thermally transmitted to the sheets is small. Therefore, ultrasonic heat may not be sufficiently transmitted to the first sheet (anvil-side sheet), and the first sheet may not be sufficiently welded to the elastic members. This improves the reliability that the first sheet is welded to the elastic members by using a heating device or ultrasonic heating.

Preferably, the manufacturing apparatus further includes an introduction device 60 for guiding and introducing elastic members F onto the anvil roll 50; and the introduction device 60 includes a guide roll 62 having a plurality of guide grooves G2 for receiving the elastic members F wound therearound and guiding the elastic members F onto the carrying grooves G of the anvil roll 50, and a regulating roll 61 for regulating a range of a contact angle θ over which the elastic members F are wound around the guide roll 62.

In this case, the contact angle over which the elastic members are in contact with the guide roll with guide grooves provided thereon can be made large, and it is possible to prevent the elastic members from coming off the guide grooves. Therefore, it is possible to stably guide the elastic members into the carrying grooves of the anvil roll. Thus, the elastic members are secured to the sheets without breaking.

Note that it is possible to even more stably guide by providing guide grooves also on the regulating roll.

Preferably, additional carrying grooves G9, separate from the carrying grooves G, are provided in the anvil roll intermittently or continuously between the ridges along a direction in which the carrying grooves G extend.

That is, preferably, carrying grooves may be provided not only on ridges but also between ridges so that the carrying grooves are provided continuously across the entire circumference of the anvil roll. In this case, the carrying grooves formed on ridges and between ridges will reliably guide the elastic members.

When the width of the ridges is less than 1 mm, even if carrying grooves are provided on ridges having a small width, the elastic members may possibly come off the carrying grooves because the elastic members move into the carrying grooves with the first sheet interposed therebetween. Particularly, when the width of the ridges is small, dynamically speaking, the elastic members are likely to be in contact with the anvil roll surface, between ridges, with the first sheet interposed therebetween, as the height to which the ridges protrude is set to be small. Therefore, the guiding of the elastic members onto the carrying grooves is likely to be unstable.

In view of this, by providing the carrying grooves not only on ridges but also between ridges, it is possible to reliably guide the elastic members.

Any feature illustrated and/or depicted in conjunction with one of the aforementioned aspects or the following embodiments may be used in the same or similar form in one or more of the other aspects or other embodiments, and/or may be used in combination with, or in place of, any feature of the other aspects or embodiments.

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

Embodiments

Prior to the description of embodiments of the stretchable sheet, an example structure of a disposable worn article using the stretchable sheet will be described.

Figure 11A:
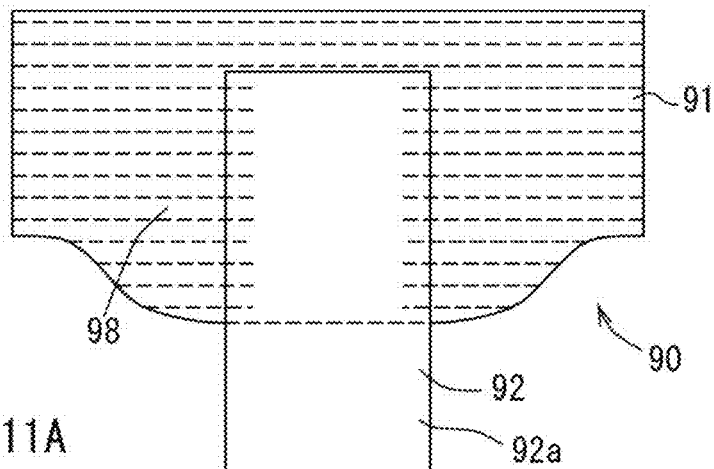
FIG. 11A is a plan view showing, flattened, an example of a worn article to which the present invention is applied.

FIG. 11A shows a worn article in a flattened state, wherein a worn article 90 includes an absorbent body 92 and a pair of, front and rear, around-torso members 91 and 91. The absorbent body 92 is provided so as to bridge between the pair of around-torso members 91 and 91, thereby forming a crotch portion 92a.

The present worn article 90 is worn while the crotch portion 92a is folded in two along a virtual line that is parallel to the girth direction X. Thus, the end portions of the pair of around-torso members 91 and 91 in the girth direction X overlap with each other.

Figure 11B:
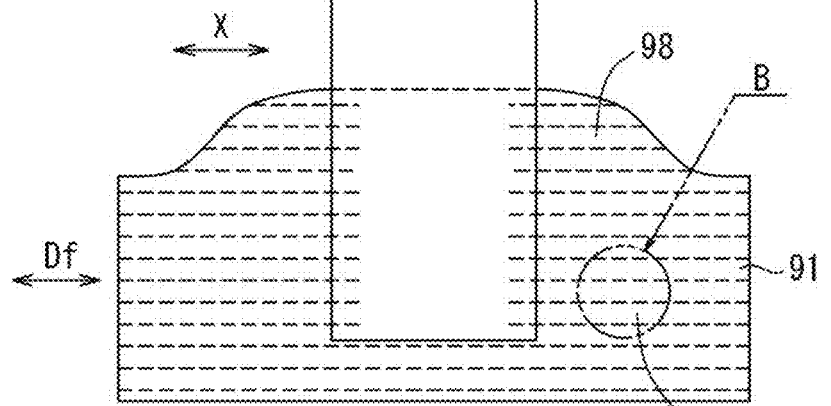
FIG. 11B is an enlarged plan view of the B part (stretchable sheet) according to Embodiment 1.
Figure 11C:
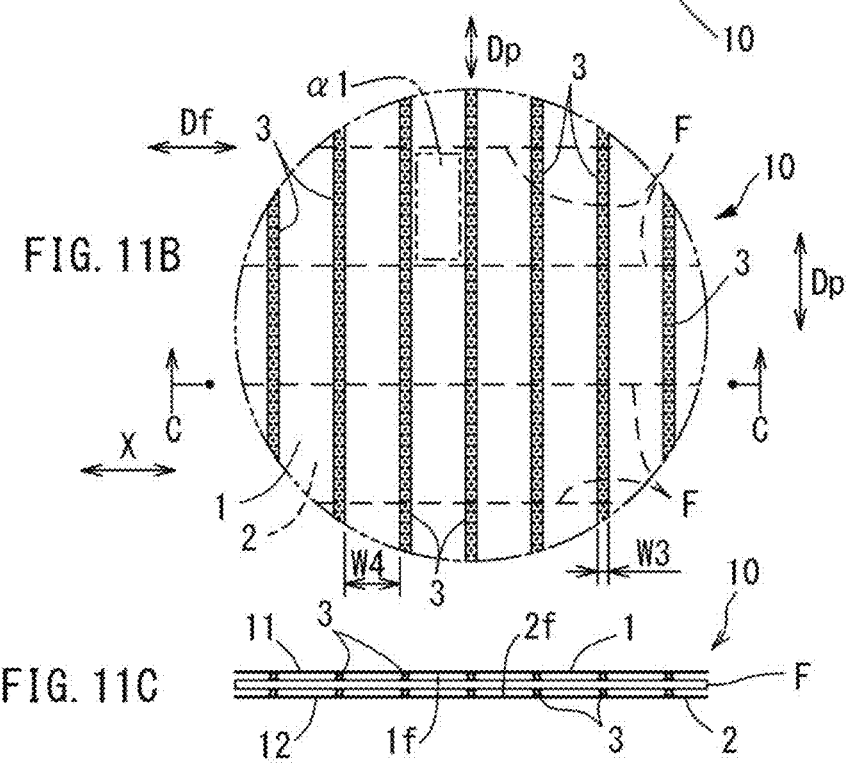
FIG. 11C is an enlarged cross-sectional view of the stretchable sheet of Embodiment 1.

The front and rear around-torso members 91 each include a stretchable sheet 10, as clearly shown in FIG. 11B and FIG. 11C. The stretchable sheet 10 includes a laminate including elastic members F and the first and second sheets 1 and 2 layered together.

The first sheet 1 and the second sheet 2 are each made of an air-permeable non-woven fabric. The elastic members F are sandwiched between the first sheet 1 and the second sheet 2, and are stretchable in the girth direction X.

The stretchable sheet 10 of the worn article 90 (FIG. 11A) has a skin-contact surface 11 to be in contact with the skin of the wearer, and a non-skin-contact surface 12 on the opposite side.

Next, Embodiment 1 of the stretchable sheet 10 will be described.

First, a state where the elastic members F are stretched will be described.

As shown in FIG. 11C, the first surfaces 1f and 2f of the pair of sheets 1 and 2 oppose each other or are in contact with each other. The plurality of elastic members F are arranged between the first surfaces 1f and 2f of the pair of sheets 1 and 2, and are arranged spaced apart from each other as indicated by broken lines in FIG. 11B.

As shown in FIG. 11B and FIG. 11C, the pair of sheets 1 and 2 are attached to each other by being welded (structure), without using an adhesive, at a plurality of attached portions 3. In the present example, the pair of sheets 1 and 2 are welded to the elastic members F at the attached portions 3, thereby securing the elastic members F to the pair of sheets 1 and 2 at the attached portions 3.

Figure 4:
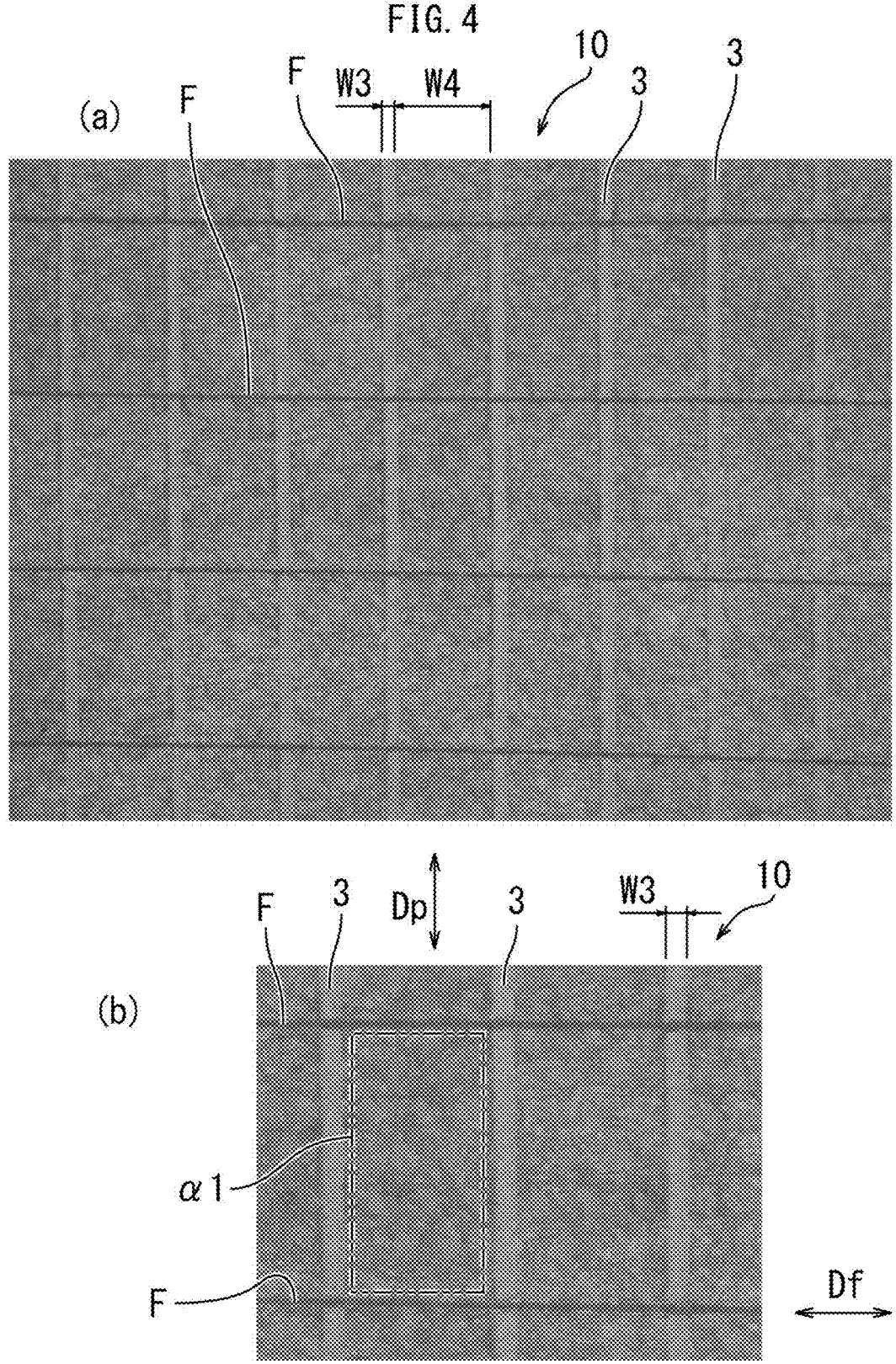
FIGS. 4(a) and 4(b) are an enlarged plan view and a more enlarged plan view, respectively, showing digital photographs of the stretchable sheet in a stretched, flattened state.
Figure 8:
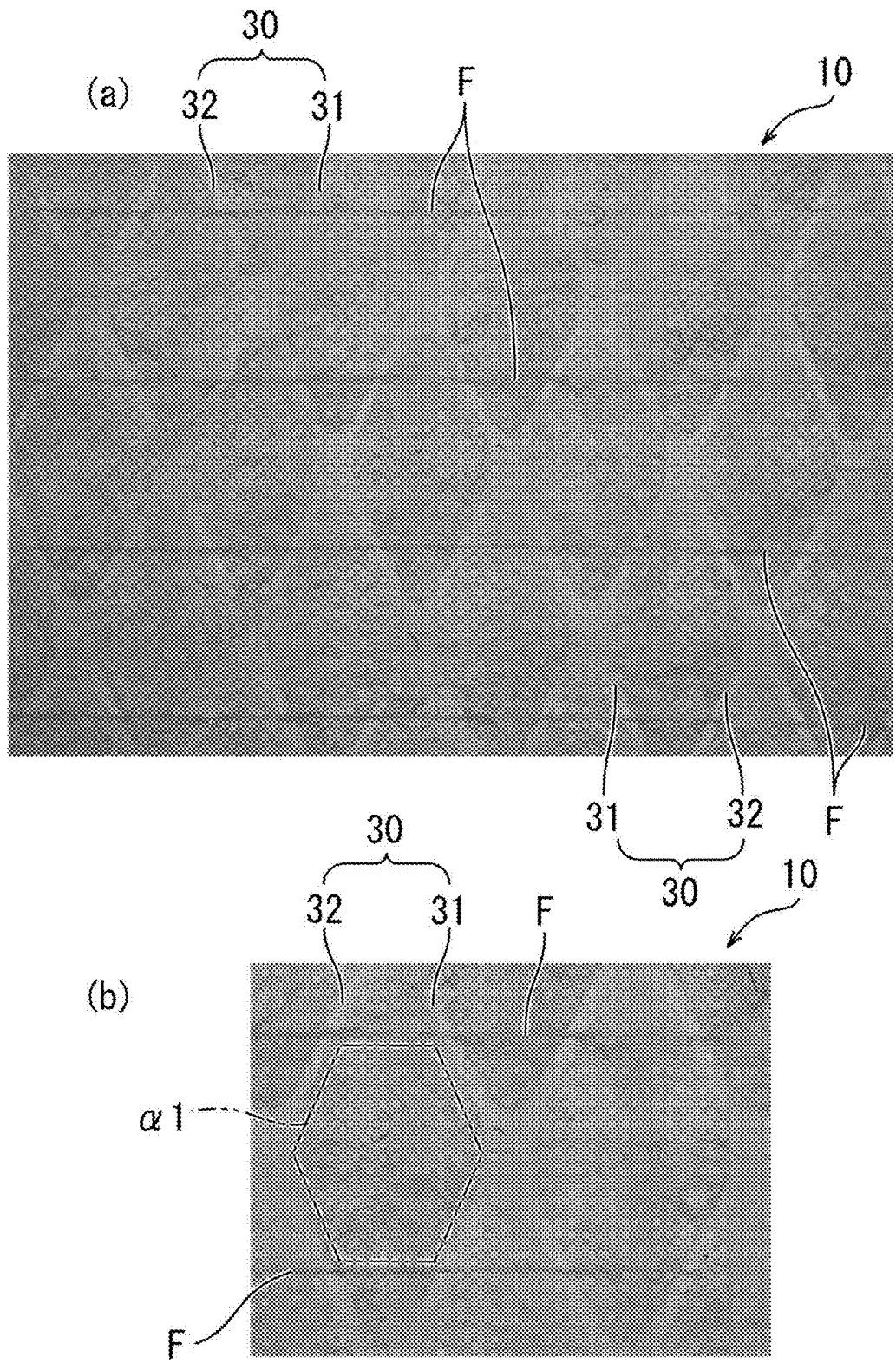
FIGS. 8(a) and 8(b) are an enlarged plan view and a more enlarged plan view, respectively, showing digital photographs of the stretchable sheet in a stretched, flattened state.

The attached portions 3 are formed (attached by a welded structure) as the pair of sheets 1 and 2 are welded together on the first surfaces 1f and 2f of the pair of sheets 1 and 2 of FIG. 11C. The attached portions 3 extend in the direction Dp that crosses (e.g., is perpendicular to) the direction of stretch Df of the elastic members F of FIGS. 4(a) and 4(b), and are spaced apart from each other in the direction of stretch Df.

The elastic members F may be line-shaped or chord-shaped. For example, as shown in FIG. 9(b), an elastic member F may be a multi-strand member, which is a bunch of rubber threads (elastic fibers) μl. The material of the rubber threads μl may be polyurethane, for example.

Due to the shrinking force of the elastic members F, the stretchable sheet 10 forms a large number of folds P when the elastic members F are shrunk, as shown in FIG. 2 and FIG. 3. The stretchable sheet 10 when the elastic members F are shrunk will now be described.

As shown in FIG. 2(b) and FIG. 3(b), the sheets 1 and 2 may each be a thermoplastic non-woven fabric including a large number of thermoplastic fibers 11 layered together, for example.

The folds P of FIG. 1(a) are formed as the pair of sheets 1 and 2 protrude in the perpendicular direction Dv between the attached portions 3 as shown in FIG. 1(a) with respect to the virtual plane Vp including the elastic members F, in a state where the elastic members F of FIG. 1(b) are shrunk.

That is, in each area α1 defined between adjacent attached portions 3 and adjacent elastic members F of FIG. 4(b), non-bonded positions of the pair of sheets 1 and 2 of FIGS. 2(a) and 2(b) that oppose each other protrude in the same perpendicular direction Dv, thereby forming a fold P. Herein, the area α1 refers to an area between attached portions 3 that is between elastic members F. On the other hand, on a cross section of FIG. 3(a) that is close to an elastic member F, the first sheet 1 forms folds P and the second sheet 2 is received by the elastic member F. Note that the second sheet 2 may be welded to the elastic member F at the attached portions 3 of FIG. 4(b). That is, the elastic members F are not welded to the sheets 1 and 2 (FIG. 3(a)) at positions other than the attached portions 3.

Note that by taking a photograph of a cross section as shown in FIG. 2, it is possible to know that the sheets 1 and 2 are non-bonded to each other and that they are welded to each other.

As shown in FIG. 4(a) and FIG. 1(b), the attached portions 3 are formed in straight lines parallel to each other so that the folds P of FIG. 1(a) are formed in straight lines parallel to each other along the attached portions 3 (FIG. 2(a)) that are parallel to each other.

As shown in the super-enlarged cross sections of FIG. 2(b) and FIG. 9(a), the first surfaces 1f and 2f of the pair of sheets 1 and 2 may be in contact with each other at at least some of the positions where they oppose each other to form the folds P, for example.

As shown in FIG. 2(a), at the folds P, the first surfaces 1f and 2f of the pair of sheets 1 and 2 may be in such close contact with each other that the boundary therebetween is obscure. Conversely, at the folds P, the first surfaces 1f and 2f of the pair of sheets 1 and 2 of FIG. 2(b) may be completely spaced apart from each other.

As shown in FIG. 4(b), the width W3 of the attached portions 3 in the direction of stretch Df is set to be 0.2 mm or more and less than 1.0 mm. In the case of the example of FIG. 4(b), W3=0.6 mm, and it can be seen that the two sheets, or the sheets and the elastic members F, are beautifully uniformly attached together at the attached portions 3.

In view of obtaining the attaching force of the attached portions 3 described above, the width W3 of the attached portions 3 is preferably 0.95 mm or less, more preferably 0.9 mm or less, and most preferably 0.85 mm or less.

Typically, the attaching force between the elastic members F and the sheets 1 and 2 will be weaker than the attaching force between the sheets 1 and 2. Therefore, if the width W3 of the attached portions 3 is too small, the attaching force between the elastic members F and the sheets 1 and 2 is likely to be insufficient.

From such a viewpoint, the width W3 of the attached portions 3 is preferably 0.3 mm or more, more preferably 0.35 mm or more, and most preferably 0.4 mm or more.

The interval between adjacent attached portions 3 of FIG. 4(a), i.e., the width W4 of the non-attached area α1, may be set to be 3 mm to 7 mm, for example, with the stretchable sheet 10 being stretched. If the width W4 is too small, the effect of the folds is not realized, and if the width W4 is too large, the folds will be higher and easier to collapse, the stretchable sheet as a whole will be thick, and there will likely be a waste of material.

Next, an example of the manufacturing apparatus of the stretchable sheet 10 will be described.

The manufacturing apparatus of FIG. 13A includes an anvil roll 50, an introduction device 60, a welding device 70, etc.

The introduction device 60 guides and introduces the elastic members F onto the anvil roll 50. The first sheet 1 is introduced onto the anvil roll 50 at a position upstream of the position of introduction of the elastic members F, and the second sheet 2 is introduced at a position downstream of the position of introduction of the elastic members F. The anvil roll 50 carries the pair of sheets 1 and 2 and the elastic members F so that the elastic members F are arranged between the pair of sheets 1 and 2.

The welding device 70, in cooperation with the anvil roll 50, welds together the pair of sheets 1 and 2, and welds the pair of sheets 1 and 2 to the elastic members F so that the elastic members F are held by the pair of sheets 1 and 2. In the present example, the welding device 70 is an ultrasonic welding device that performs the welding with an ultrasonic energy.

The welding device 70 gives a vibration energy to a plurality of attached portions 3 of the two non-woven fabric sheets 1 and 2 of the stretchable sheet 10 of FIG. 11C, thereby welding together the two non-woven fabric sheets 1 and 2 and the elastic members F.

More specifically, the anvil roll 50 of FIG. 14 has a large number of ridges 52, which correspond to the attached portions 3 (FIG. 4), on a circumferential surface 51. The ridges 52 extend in the width direction S of the anvil roll 50.

The welding device 70 of FIG. 13A includes the horn 71. An ultrasonic energy is given to the horn 71, and the horn 71 opposes a ridge 52 of FIG. 13C with the pair of sheets 1 and 2 and the elastic members F interposed therebetween.

In FIG. 13C, the width W1 of the horn 71 along the flow direction of the sheets 1 and 2 may be greater than the width W2 of the ridges (each ridge) 52. The setting may be such that a plurality of ridges 52 oppose the horn 71 at the same time on a temporary or non-temporary basis.

As shown in FIG. 13C, the width W2 of the ridges 52 is set to be 0.2 mm or more and less than 1.0 mm. In the case of this example, W3=0.6 mm, and it can be seen that the two sheets, or the sheets and the elastic members F, are beautifully uniformly attached together at the attached portions 3, as shown in FIG. 4(b).

In view of preventing breakage of elastic members at the attached portions 3 described above, the width W2 of the ridges 52 of FIG. 13C is preferably 0.95 mm or less, more preferably 0.9 mm or less, and most preferably 0.85 mm or less.

On the other hand, when the width W2 of the ridges 52 is too small, the durability of the ridges 52 may possibly lower significantly due to the repetitive stress from the horn 71 hitting the ridges 52.

From such a viewpoint, the width W2 of the ridges 52 is preferably 0.3 mm or more, more preferably 0.35 mm or more, and most preferably 0.4 mm or more.

On the other hand, the distance W40 between adjacent ridges 52 and 52 of FIG. 13C corresponds to the width W4 (FIG. 4(a)) of the non-attached area α1. Therefore, the distance W40 may be set to be 3 mm to 20 mm, for example.

Figure 15:
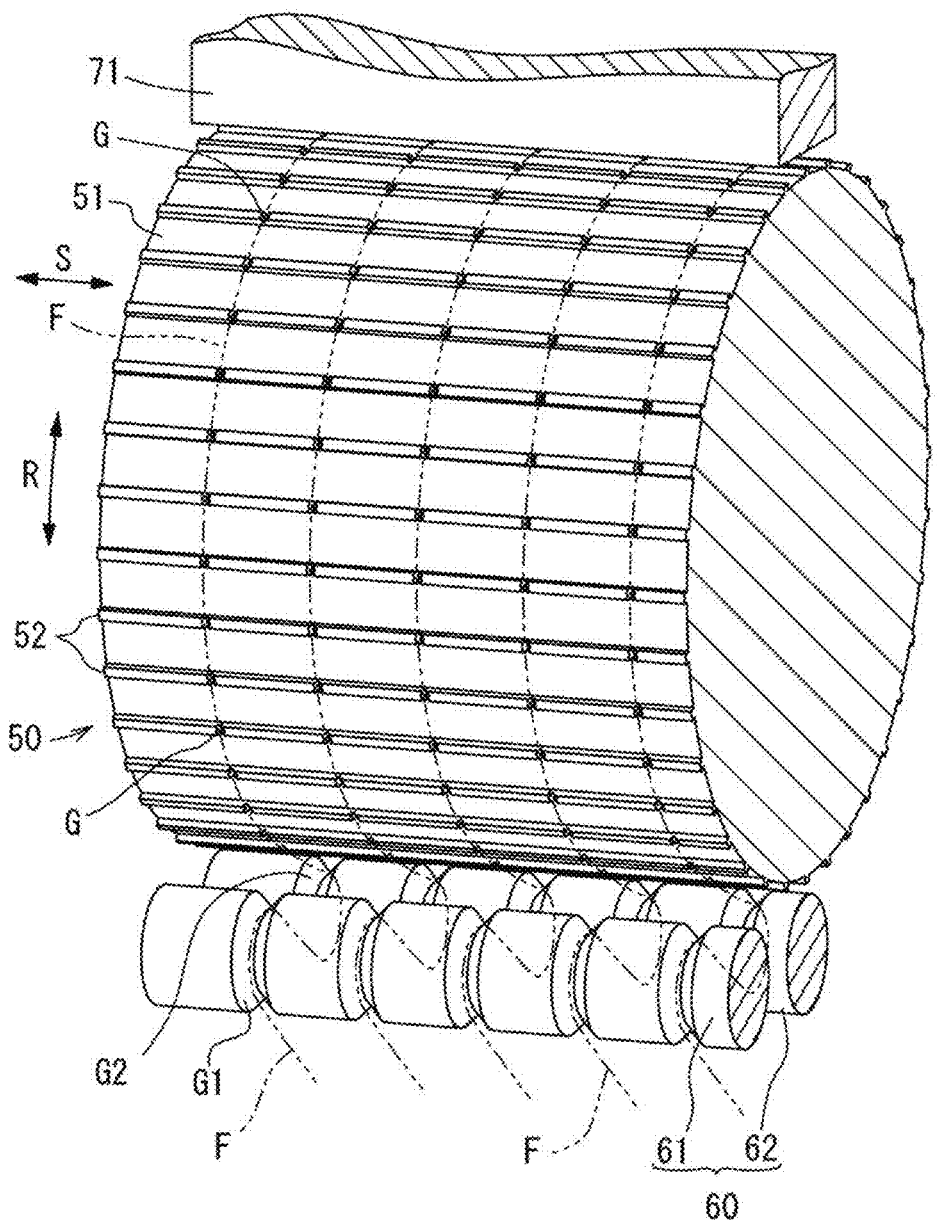
FIG. 15 is a schematic perspective view of the anvil roll as seen from below.

As shown in FIG. 14 and FIG. 15, the anvil roll 50 has a plurality of carrying grooves G. The carrying grooves G are formed in the ridges 52, extend in the circumferential direction R of the anvil roll 50 so as to cross the ridges 52, and carry the elastic members F with the first sheet 1 (FIG. 13A) and the elastic members F being held in the carrying grooves G. The carrying grooves G are depressed toward the center in the radial direction of the anvil roll 50.

Figure 16A:
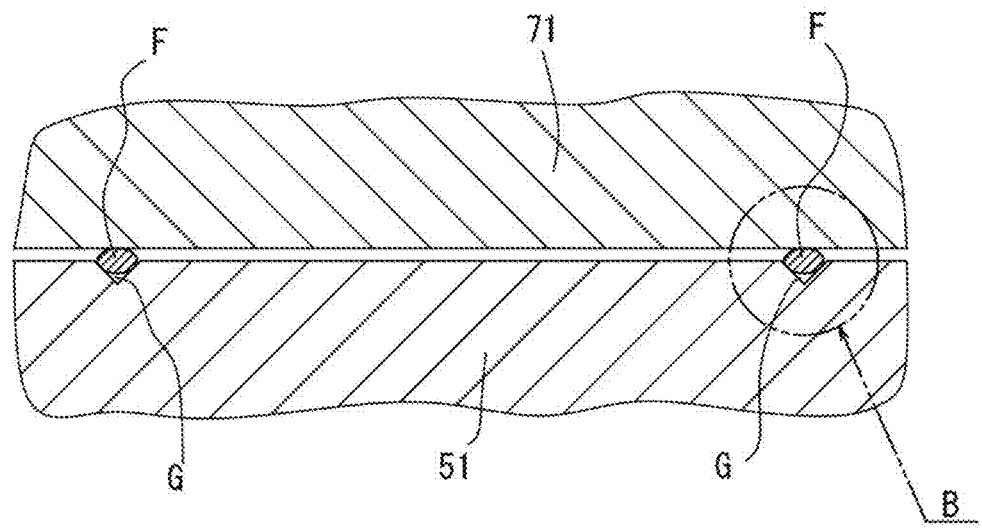
FIG. 16A is an enlarged cross-sectional view of the horn and the anvil roll taken along a ridge position of the anvil roll.
Figure 16B:
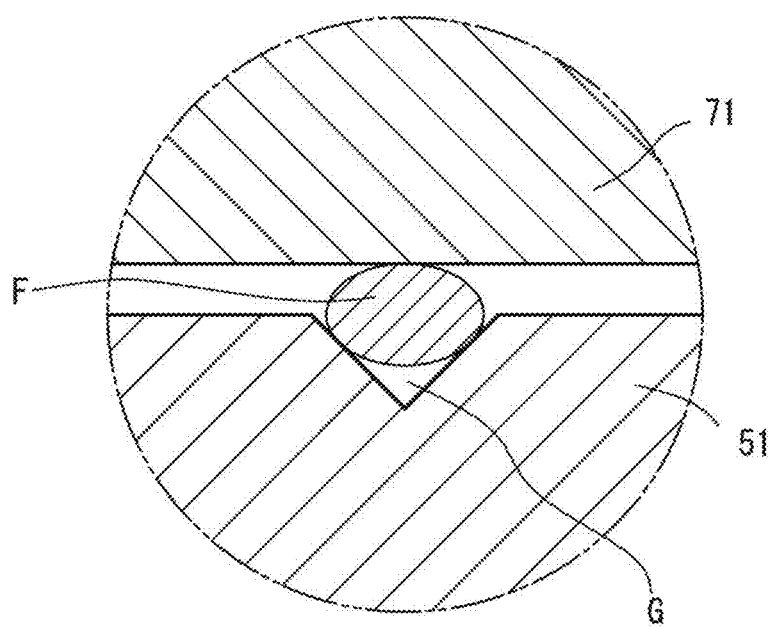
FIG. 16B is a more enlarged cross-sectional view thereof.

As shown in FIG. 16A and FIG. 16B, the size of the carrying grooves G may be set so that the elastic members F are partly accommodated in the grooves with the remaining portion thereof lying outside the grooves. The cross-sectional area of the carrying grooves G may be smaller than the cross-sectional area of the elastic members F in natural length.

Note that although the sheets 1 and 2 are not shown in FIG. 13C to FIG. 16B, the sheets 1 and 2 are arranged so as to sandwich the elastic members F therebetween as schematically shown in FIG. 9(c).

The introduction device 60 of FIG. 13A includes a first roll (regulating roll) 61 and a second roll (guide roll) 62. The first and second rolls 61 and 62 of FIG. 14 may include a plurality of first and second guide grooves G1 and G2, respectively. The elastic members F are wound around the first guide grooves G1, and the first guide grooves G1 guide the elastic members F. The elastic members F, which have been guided out of the first guide grooves G1 of the first roll 61, are wound around the second guide grooves G2 of FIG. 15, and the second guide grooves G2 guide the elastic members F onto the carrying grooves G of the anvil roll 50.

In FIG. 13A, the regulating roll (first roll) 61 regulates the range of the contact angle θ over which the elastic members F are wound around the guide roll (second roll) 62. Typically, the contact angle θ is preferably about 90° to about 270°. This is for preventing the elastic members F from coming off the second guide grooves G2.

The first and second rolls 61 and 62 may be free rollers, or may be rotated in sync with the anvil roll 50.

In FIG. 13A, the manufacturing apparatus may include a tension roller TR. The tension roller TR is provided along the carrying path of the second sheet 2, and is provided upstream, in the carrying direction of the second sheet 2, of the position at which welding is done by the horn 71.

With the tension roller TR, the tension in the carrying direction of the second sheet 2 being carried toward the welding position between the horn 71 and the anvil roll 50 is higher than the tension of the first sheet 1 in the carrying direction. Such a function of the tension roller TR may be realized by a mechanical structure well known in the art or may be realized by an electronic control.

In FIG. 13A, the manufacturing apparatus may further include a heating device 59. The heating device 59 may be a heater for increasing the temperature of the anvil roll 50, or may be a hot air blower for blowing a warm air or a hot air onto the first sheet 1 at a position upstream of the welding position. Note that the heating device may be a different welding device provided at a position downstream of the welding position.

Next, an example of a method for manufacturing the stretchable sheet 10 will be described.

As shown in FIG. 13A, the first sheet 1 is introduced onto an upstream portion of the anvil roll 50. The elastic members F are introduced from the introduction device 60 onto the first sheet 1, which has been introduced onto the anvil roll 50. The elastic members F are carried while being held, together with the first sheet 1 (FIG. 13A), in the carrying grooves G of FIG. 13C. On the other hand, the second sheet 2 of FIG. 13A is introduced onto a position of the anvil roll 50 that opposes the horn 71.

When the first sheet 1, the elastic members F and the second sheet 2 pass through between the horn 71 and the ridge 52, the horn 71 ultrasonically vibrates toward the anvil roll 50. Thus, the sheets 1 and 2 are welded to each other, and the sheets 1 and 2 are welded to the elastic members F. Thus, the stretchable sheet 10 is produced.

The manufacture of the stretchable sheet 10 is performed in a flattened state where the elastic members F, the first sheet 1 and the second sheet 2 of FIG. 13A are under a tension in the carrying direction. Therefore, immediately after welding by the horn 71, the stretchable sheet 10 is produced in a flattened state as shown in FIGS. 4(a) and 4(b), and no folds appear on the stretchable sheet 10 in this state.

Then, the stretchable sheet 10 of FIG. 13A is carried downstream and is brought into a state where it is no longer under a tension in the carrying direction. In this state, folds P appear on the stretchable sheet 10 as shown in FIG. 13B.

The folds P thus produced may protrude exposed on a skin-contact surface 98 of FIG. 11A, or may protrude exposed on a non-skin-contact surface opposite thereto.

Next, another example will be described.

FIG. 5 to FIG. 8, FIG. 10 and FIG. 12A show Embodiment 2.

In the present embodiment, as shown in FIGS. 8(a) and 8(b) and FIG. 12A, the attached portions 3 include a plurality of first attached portions 31 and a plurality of second attached portions 32. The first attached portions 31 extend in the first direction D1 crossing the direction of stretch Df of the elastic members F. The second attached portions 32 extend in the second direction D2 crossing the direction of stretch Df and the first direction D1.

As shown in FIG. 12A, in the present example, the width W3 of the attached portions 3 in the direction of stretch Df is measured diagonally with respect to the direction in which the attached portions 3 extend. The width W3 may be larger at positions where the first attached portion 31 and the second attached portion 32 intersect.

In the present example, in the state of FIG. 12A and FIG. 8(b) where the elastic members F are stretched, the area α1 is defined by the elastic members F and the first and second attached portions 31 and 32.

In the present example, as shown in FIGS. 5(a) and 5(b), the folds P appear in both directions of the perpendicular direction Dv. That is, as shown on an enlarged scale in FIGS. 6(a) and 6(b) and FIG. 10, the folds P appear in the areas α1 (FIG. 8) in one direction and in the other direction of the perpendicular direction Dv.

Figure 10:
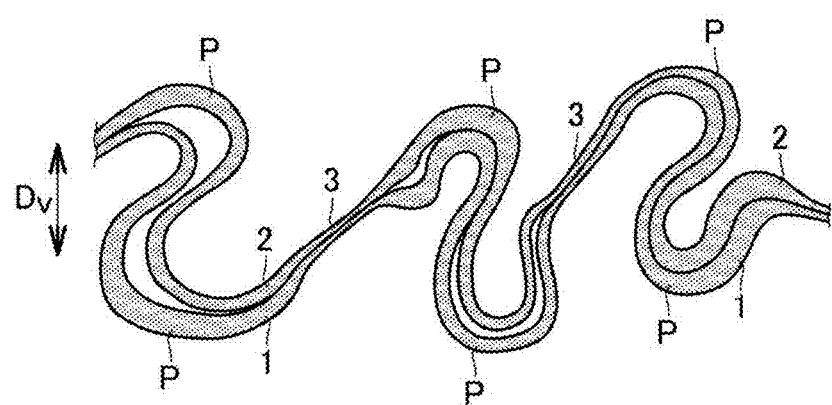
FIG. 10 is a cross-sectional view showing a drawing of the cross section of the stretchable sheet of FIG. 6(b).

However, also in such a case, the opposing positions of the pair of sheets 1 and 2 of FIGS. 6(a) and 6(b) and FIG. 10 protrude in the same perpendicular direction Dv in each area α1 of FIG. 8(b), thus forming the folds P.

Also in the present example, on a cross section of FIGS. 7(a) and 7(b) that is close to the elastic members F, one of the sheets 1 and 2 may form the folds P and the other one of the sheets 1 and 2 may be stuck on the elastic members F as if by tangling with the elastic members F.

FIG. 12B shows Embodiment 3.

Each attached portion 3 may be formed in a wave shape as in this example. In this case, although the attached portions 3 do not intersect each other, folds P of a similar shape to Embodiment 2 of FIG. 12A will be formed.

In the examples of FIG. 11B to FIG. 12B, each attached portion 3 is continuous and crosses the elastic members F, and the pair of sheets 1 and 2 (FIG. 11C) are welded to the elastic members F at positions where the elastic members F extend.

However, each attached portion 3 may be non-continuous as shown in FIG. 12C and FIG. 12D. The pair of sheets 1 and 2 do not need to be welded to the elastic members F at positions where the elastic members F of FIG. 12C extend. That is, the attached portions 3 and the elastic members F do not need to overlap with each other, and the attached portions 3 may extend continuously or intermittently.

In the case of the example of FIG. 12C, the opposite ends of the elastic members F may be secured to the first and second sheets by bonding or welding. By bringing the attached portions 3 closer to the elastic members F, fibers of the non-woven fabric may get tangled with the elastic members F, and the elastic members F can thus be secured.

That is, the attached portions 3 may hold the elastic members F so that the elastic members F are not close to each other or too far away from each other, and the elastic members F do not always need to be secured to the sheets.

FIG. 17A and FIG. 17B show another example of the anvil roll 50.

In this example, in addition to the carrying grooves G provided in the ridges 52, additional carrying grooves G9 are provided between adjacent ridges 52 and 52. That is, the carrying grooves G and the additional carrying grooves G9 are provided continuously in the circumferential direction R of the anvil roll 50. Note that the additional carrying grooves G9 may be provided only in the middle portion between adjacent ridges 52 and 52, without being provided in an area that is on opposite sides of, and in contact with, each ridge 52.

The guide grooves G2 may be provided only on the second roll 62 without providing guide grooves on the first roll 61.

FIG. 18 shows still another example.

In this example, an additional welding device 70A as a heating device is provided, in addition to the welding device 70. The additional welding device 70A re-welds the attached portions 3 of the stretchable sheet 10, which have been welded by the welding device 70.

The second sheet 2 side of the stretchable sheet 10 is in contact with an anvil roll 50A of the additional welding device 70A, and the first sheet 1 side of the stretchable sheet 10 is in contact with the horn 71A. Thus, the horn 71 of the welding device 70 heats the attached portions 3 from the second sheet side, and the horn 71A of the additional welding device 70A heats the attached portions 3 from the first sheet side.

Note that a nip roll NR may be provided for nipping the first sheet 1, the elastic members F and the second sheet 2 between the nip roll NR and the anvil roll 50. The nip roll NR is provided upstream of the welding device 70. Such a nip roll NR may be provided in the manufacturing apparatus of FIG. 13A.

FIG. 19 and FIG. 20 show another example of the introduction device 60.

The introduction device 60 of FIG. 19 includes the first roll 61 for receiving the elastic members F from upstream, the second roll 62 for receiving the elastic members F from the first roll 61, and a hold-down roll 63 that is in contact with the second roll 62.

A number of relatively wide and deep first guide grooves G1, in accordance with the number of elastic members F (FIG. 19), are provided on the first roll 61 of FIG. 20. The first guide grooves G1 guide the elastic members F, which have been received from the upstream side, to the centers of the grooves. Note that there is a slight gap between the circumferential surfaces of the first roll 61 and the second roll 62.

Narrower and shallower second guide grooves G2 than the first guide grooves G1 of the first roll 61 are formed on the second roll 62, and the second guide grooves G2 are formed so as to correspond to the first guide grooves G1 of the first roll 61. The second guide grooves G2 of the second roll 62 may be set to a width that is greater than the thickness of the stretched elastic members F (FIG. 19) being carried.

The elastic members F, which have been passed over to the second roll 62 from the first roll 61, move into the second guide grooves G2 of the second roll 62 and are held by the hold-down roll 63, thus preventing the elastic members F from coming off the second guide grooves G2. Therefore, the elastic members F of FIG. 20 are accurately guided onto the anvil roll 50.

Other structures and manufacturing methods of worn articles 90 of other embodiments are similar to those of Embodiment 1 described above, and the same portions and like portions are denoted by like reference numerals and will not be described in detail below.

While preferred embodiments have been described above with reference to the drawings, various obvious changes and modifications will readily occur to those skilled in the art upon reading the present specification.

For example, the stretchable sheet can be applied to products other than worn articles.

Thus, such changes and modifications are deemed to fall within the scope of the present invention, which is defined by the appended claims.

INDUSTRIAL APPLICABILITY

The present invention is applicable to a stretchable sheet that can suitably be used in diaper-type and pants-type disposable worn articles, and a manufacturing apparatus therefor.

REFERENCE SIGNS LIST 1, 2: Pair of sheets, 10: Stretchable sheet, 1f, 2f: First surface
3: Attached portion, 31: First attached portion, 32: Second attached portion
50: Anvil roll, 51: Circumferential surface, 52: Ridge, 50A: Additional anvil roll
59: Heating device
60: Introduction device, 61: First roll (regulating roll), 62: Second roll (guide roll)
70: Welding device, 71: Horn, 70A: Additional welding device, 71A: Additional horn
D1: First direction, D2: Second direction, Df: Direction of stretch, Dp: Crossing direction
F: Elastic member
G: Carrying groove, G9: Additional carrying groove, G1: First guide groove, G2: Second guide groove
S: Width direction
NR: Nip roll, TR: Tension roller
P: Fold, Vp: Virtual plane, W1 to W4: Width
α1: Area, θ: Contact angle

The invention claimed is:

1. A stretchable sheet comprising:
a pair of sheets whose first surfaces oppose each other or are in contact with each other;
a plurality of elastic members that are arranged between the first surfaces of the pair of sheets and are arranged spaced apart from each other;
a plurality of attached portions, wherein the first surfaces of the pair of sheets are attached to each other by a welding construction without using an adhesive, at the attached portions; the attached portions hold the elastic members; the attached portions extend in a direction crossing a direction of stretch of the elastic members; and the attached portions are spaced apart from each other in the direction of stretch at positions where the attached portions cross the elastic members; and a plurality of folds that appear between the attached portions in a state where the elastic members are shrunk, wherein a width of the attached portions in the direction of stretch is set to be 0.2 mm or more and less than 1.0 mm, the folds are formed as the pair of sheets protrude, between the attached portions, with respect to a virtual plane that includes the elastic members; and in an area defined between adjacent attached portions of the attached portions and adjacent elastic members of the elastic members, non-bonded positions of the pair of sheets that oppose each other protrude in the same direction, thereby forming a fold of the folds.

2. The stretchable sheet according to claim 1, wherein at least one of the pair of sheets is attached to the elastic members by a welding construction at the attached portions.

3. The stretchable sheet according to claim 1, wherein:

the attached portions are formed in straight lines parallel to each other; and the folds are formed in straight lines parallel to each other along the attached portions that are parallel to each other.

4. The stretchable sheet according to claim 1, wherein:

the attached portions include a plurality of first attached portions that extend in a first direction crossing the direction of stretch of the elastic members, and a plurality of second attached portions that extend in a second direction crossing the direction of stretch and the first direction; and the area is defined by the elastic members, the first attached portions and the second attached portions.

5. A worn article comprising the stretchable sheet according to claim 1, wherein:

the worn article has a skin-contact surface to be in contact with a skin of a wearer, and a non-skin-contact surface that is opposite to the skin-contact surface; and the folds protrude on the non-skin-contact surface.

6. A worn article comprising the stretchable sheet according to claim 1, wherein:

the worn article has a skin-contact surface to be in contact with a skin of a wearer, and a non-skin-contact surface that is opposite to the skin-contact surface; and the folds protrude on the skin-contact surface.

* * * * *